(12) United States Patent
Wenderow et al.

(10) Patent No.: US 12,171,955 B2
(45) Date of Patent: *Dec. 24, 2024

(54) REMOTE CATHETER PROCEDURE SYSTEM

(71) Applicant: Corindus, Inc., Waltham, MA (US)

(72) Inventors: Tal Wenderow, Newton, MA (US); Thomas Bromander, Andover, MA (US)

(73) Assignee: Siemens Healthineers Endovascular Robotics Inc, Newton, MA (US)

( * ) Notice: Subject to any disclaimer, the term of this patent is extended or adjusted under 35 U.S.C. 154(b) by 753 days.

This patent is subject to a terminal disclaimer.

(21) Appl. No.: 16/739,032

(22) Filed: Jan. 9, 2020

(65) Prior Publication Data

US 2020/0316340 A1    Oct. 8, 2020

Related U.S. Application Data

(63) Continuation of application No. 15/372,985, filed on Dec. 8, 2016, now Pat. No. 10,561,821, which is a (Continued)

(51) Int. Cl.
*A61M 25/01* (2006.01)
*A61B 34/00* (2016.01)
(Continued)

(52) U.S. Cl.
CPC ......... *A61M 25/0105* (2013.01); *A61B 34/30* (2016.02); *A61B 34/74* (2016.02);
(Continued)

(58) Field of Classification Search
CPC ............ A61M 25/0105; A61M 25/104; A61B 34/30; A61B 34/74; A61B 2034/301; A61B 2090/376
See application file for complete search history.

(56) References Cited

U.S. PATENT DOCUMENTS 2,718,598 A    9/1955 Graf
3,147,953 A    9/1964 Arth
(Continued)

FOREIGN PATENT DOCUMENTS

EP    0329492 A2    8/1989
EP    0331944 A1    9/1989
(Continued)

OTHER PUBLICATIONS

Beyar et al., Remote-Control Percutaneous Coronary Interventions: Concept, Validation, and First-in-Humans Pilot Clinical Trial, Journal of the American College of Cardiology, Sep. 24, 2005, 5 pages.

*Primary Examiner* — Richard G Louis

(57) ABSTRACT

A catheter procedure system including a bedside system and a remote workstation is provided. The bedside system includes a catheter including an expandable percutaneous intervention device, a robotic catheter system configured to move the catheter, and an inflation device configured to cause expansion of the expandable percutaneous intervention device. The remote workstation includes a user interface configured to receive a at least first user input and a second user input and a control system operatively coupled to the user interface for remotely controlling both the robotic catheter system and the inflation device. The remote workstation includes a monitor configured to display information related to the expandable percutaneous intervention device. The control system controls the robotic catheter system to move the catheter based upon at least the first user input and controls the inflation device to cause expansion of the expandable percutaneous intervention device based upon at least the second user input.

16 Claims, 16 Drawing Sheets

Related U.S. Application Data continuation of application No. 13/152,168, filed on Jun. 2, 2011, now Pat. No. 9,545,497, which is a continuation of application No. PCT/US2009/067540, filed on Dec. 10, 2009.

(60) Provisional application No. 61/122,263, filed on Dec. 12, 2008.

(51) Int. Cl.
  *A61B 34/30* (2016.01)
  *A61B 90/00* (2016.01)
  *A61M 25/10* (2013.01)

(52) U.S. Cl.
  CPC .......... *A61B 2034/301* (2016.02); *A61B 2090/376* (2016.02); *A61M 25/104* (2013.01)

(56) References Cited

U.S. PATENT DOCUMENTS

| | | |
|---|---|---|
| 3,308,297 A | 3/1967 | Mansker |
| 4,254,341 A | 3/1981 | Herr et al. |
| 4,382,184 A | 5/1983 | Wernikoff |
| 4,581,538 A | 4/1986 | Lenhart |
| 4,965,456 A | 10/1990 | Huettenrauch et al. |
| 4,977,588 A | 12/1990 | Van Der Ende |
| 5,049,147 A | 9/1991 | Danon |
| 5,090,044 A | 2/1992 | Kobayashi |
| 5,139,473 A | 8/1992 | Bradshaw et al. |
| 5,171,299 A | 12/1992 | Heitzmann et al. |
| 5,185,778 A | 2/1993 | Magram |
| 5,300,027 A | 4/1994 | Foote et al. |
| 5,343,391 A | 8/1994 | Mushabac |
| 5,377,678 A | 1/1995 | Dumoulin et al. |
| 5,425,382 A | 6/1995 | Golden et al. |
| 5,434,775 A | 7/1995 | Sims et al. |
| 5,464,023 A | 11/1995 | Viera |
| 5,486,192 A | 1/1996 | Walinsky et al. |
| 5,487,734 A | 1/1996 | Thorne et al. |
| 5,492,131 A | 2/1996 | Galel |
| 5,578,014 A | 11/1996 | Erez et al. |
| 5,584,078 A | 12/1996 | Saboory |
| 5,623,943 A | 4/1997 | Hackett et al. |
| 5,690,645 A | 11/1997 | Van Erp |
| 5,706,827 A | 1/1998 | Ehr et al. |
| 5,821,920 A | 10/1998 | Rosenberg et al. |
| 5,842,987 A | 12/1998 | Sahadevan |
| 5,851,182 A | 12/1998 | Sahadevan |
| 5,851,210 A * | 12/1998 | Torossian ............... A61F 2/958 606/198 |
| 5,882,333 A | 3/1999 | Schaer et al. |
| 5,891,089 A * | 4/1999 | Katz .................. A61M 25/104 606/192 |
| 5,957,941 A | 9/1999 | Ream |
| 5,981,964 A | 11/1999 | McAuley et al. |
| 6,004,276 A | 12/1999 | Wright et al. |
| 6,013,038 A | 1/2000 | Pflueger |
| 6,048,300 A | 4/2000 | Thornton et al. |
| 6,083,170 A | 7/2000 | Ben-Haim |
| 6,096,004 A | 8/2000 | Meglan et al. |
| 6,126,647 A | 10/2000 | Posey et al. |
| 6,171,234 B1 | 1/2001 | White et al. |
| 6,266,552 B1 | 7/2001 | Slettenmark |
| 6,285,898 B1 | 9/2001 | Ben-Haim |
| 6,351,513 B1 | 2/2002 | Bani-Hashemi et al. |
| 6,375,471 B1 | 4/2002 | Wendlandt et al. |
| 6,447,504 B1 | 9/2002 | Ben-Haim et al. |
| 6,499,163 B1 | 12/2002 | Stensby |
| 6,554,472 B1 | 4/2003 | Dietz et al. |
| 6,705,990 B1 | 3/2004 | Gallant et al. |
| 6,726,675 B1 * | 4/2004 | Beyar ................ A61M 25/0113 600/137 |
| 6,740,103 B2 | 5/2004 | Hall et al. |
| 6,770,066 B1 | 8/2004 | Weaver et al. |
| 6,878,106 B1 | 4/2005 | Herrmann |
| 7,112,811 B2 | 9/2006 | Lemer |
| 7,276,044 B2 | 10/2007 | Ferry et al. |
| 7,608,847 B2 | 10/2009 | Rees |
| 7,615,042 B2 | 11/2009 | Beyar et al. |
| 7,697,972 B2 | 4/2010 | Verard et al. |
| D626,250 S | 10/2010 | Wenderow et al. |
| 7,887,549 B2 | 2/2011 | Wenderow et al. |
| D680,645 S | 4/2013 | Murphy et al. |
| 2001/0016726 A1* | 8/2001 | Dubrul ................. A61M 25/10 604/509 |
| 2002/0099254 A1* | 7/2002 | Movahed ............ A61M 1/3621 600/4 |
| 2002/0109107 A1 | 8/2002 | Goldstein |
| 2002/0168618 A1 | 11/2002 | Anderson et al. |
| 2002/0177789 A1 | 11/2002 | Ferry et al. |
| 2003/0069719 A1 | 4/2003 | Cunningham et al. |
| 2003/0078003 A1 | 4/2003 | Hunter et al. |
| 2003/0088209 A1 | 5/2003 | Chiu et al. |
| 2003/0176770 A1 | 9/2003 | Merril et al. |
| 2003/0199848 A1 | 10/2003 | Ledesma et al. |
| 2004/0044279 A1 | 3/2004 | Lewin et al. |
| 2004/0064086 A1 | 4/2004 | Gottlieb et al. |
| 2004/0068173 A1 | 4/2004 | Viswanathan |
| 2004/0097805 A1* | 5/2004 | Verard .................. A61B 34/20 600/428 |
| 2004/0113498 A1 | 6/2004 | Kroenke |
| 2004/0138548 A1 | 7/2004 | Strommer et al. |
| 2004/0254566 A1 | 12/2004 | Plicchi et al. |
| 2005/0222554 A1 | 10/2005 | Wallace et al. |
| 2005/0245846 A1 | 11/2005 | Casey |
| 2005/0256398 A1 | 11/2005 | Hastings et al. |
| 2005/0256504 A1 | 11/2005 | Long et al. |
| 2005/0277851 A1 | 12/2005 | Whittaker et al. |
| 2006/0041181 A1 | 2/2006 | Viswanathan et al. |
| 2006/0064059 A1* | 3/2006 | Gelfand ............... A61B 5/0215 604/500 |
| 2007/0043338 A1 | 2/2007 | Moll et al. |
| 2007/0083193 A1 | 4/2007 | Werneth et al. |
| 2007/0103437 A1 | 5/2007 | Rosenberg |
| 2007/0106247 A1 | 5/2007 | Burnett et al. |
| 2007/0118079 A1 | 5/2007 | Moberg et al. |
| 2007/0124002 A1 | 5/2007 | Estes et al. |
| 2007/0142749 A1 | 6/2007 | Khatib et al. |
| 2007/0185486 A1 | 8/2007 | Hauck et al. |
| 2007/0197896 A1 | 8/2007 | Moll et al. |
| 2007/0250097 A1 | 10/2007 | Weitzner et al. |
| 2007/0276216 A1 | 11/2007 | Beyar et al. |
| 2008/0009791 A1 | 1/2008 | Cohen et al. |
| 2008/0027313 A1 | 1/2008 | Shachar |
| 2008/0045827 A1* | 2/2008 | Rongen ................ A61B 6/504 600/407 |
| 2008/0059598 A1 | 3/2008 | Garibaldi et al. |
| 2008/0082109 A1 | 4/2008 | Moll et al. |
| 2008/0114267 A1 | 5/2008 | Lloyd et al. |
| 2008/0139915 A1 | 6/2008 | Dolan et al. |
| 2008/0167750 A1 | 7/2008 | Stahler et al. |
| 2008/0172120 A1* | 7/2008 | Fenn .................. A61M 25/1002 623/1.12 |
| 2008/0177203 A1 | 7/2008 | Von Jako |
| 2008/0217564 A1 | 9/2008 | Beyar et al. |
| 2009/0012533 A1 | 1/2009 | Barbagli et al. |
| 2009/0105639 A1 | 4/2009 | Weitzner et al. |
| 2009/0110152 A1 | 4/2009 | Manzke et al. |
| 2009/0131955 A1 | 5/2009 | Wenderow et al. |
| 2009/0137952 A1 | 5/2009 | Ramamurthy et al. |
| 2009/0138025 A1 | 5/2009 | Stahler et al. |
| 2009/0171152 A1* | 7/2009 | Aoki ................ A61B 1/00147 600/114 |
| 2009/0221958 A1 | 9/2009 | Beyar et al. |
| 2009/0247944 A1 | 10/2009 | Kirschenman et al. |
| 2010/0069833 A1 | 3/2010 | Wenderow et al. |
| 2010/0076308 A1 | 3/2010 | Wenderow et al. |
| 2010/0076309 A1 | 3/2010 | Wenderow et al. |
| 2010/0076310 A1 | 3/2010 | Wenderow et al. |

(56) References Cited

U.S. PATENT DOCUMENTS

2011/0144658 A1 6/2011 Wenderow et al.
2011/0152882 A1 6/2011 Wenderow et al.

FOREIGN PATENT DOCUMENTS

| | | |
|---|---|---|
| EP | 0554986 B1 | 7/1996 |
| EP | 0590268 B1 | 7/1998 |
| EP | 0970663 A1 | 1/2000 |
| EP | 1415660 A1 | 5/2004 |
| EP | 1442720 A1 | 8/2004 |
| EP | 1504713 B1 | 7/2008 |
| WO | 2001074252 A2 | 10/2001 |
| WO | 2002009571 A2 | 2/2002 |
| WO | 2006120666 A1 | 11/2006 |
| WO | 2009137410 A1 | 11/2009 |
| WO | 2010025336 A1 | 3/2010 |
| WO | 2010025338 A1 | 3/2010 |
| WO | 2010068783 A1 | 6/2010 |
| WO | 2010107916 A1 | 9/2010 |
| WO | 2011046874 A1 | 4/2011 |

\* cited by examiner

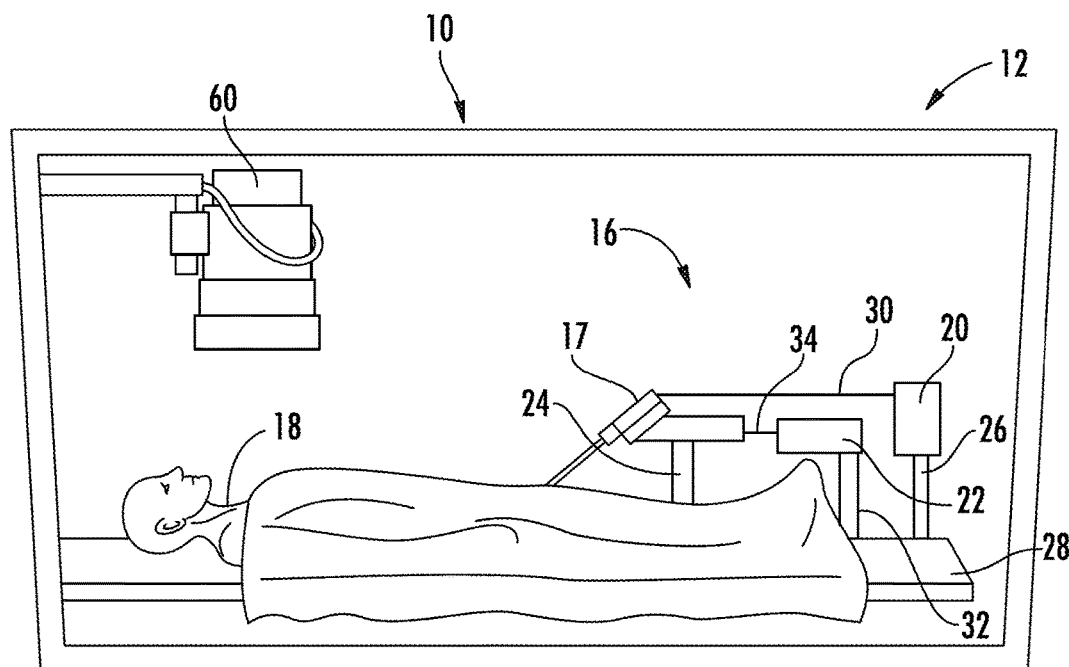
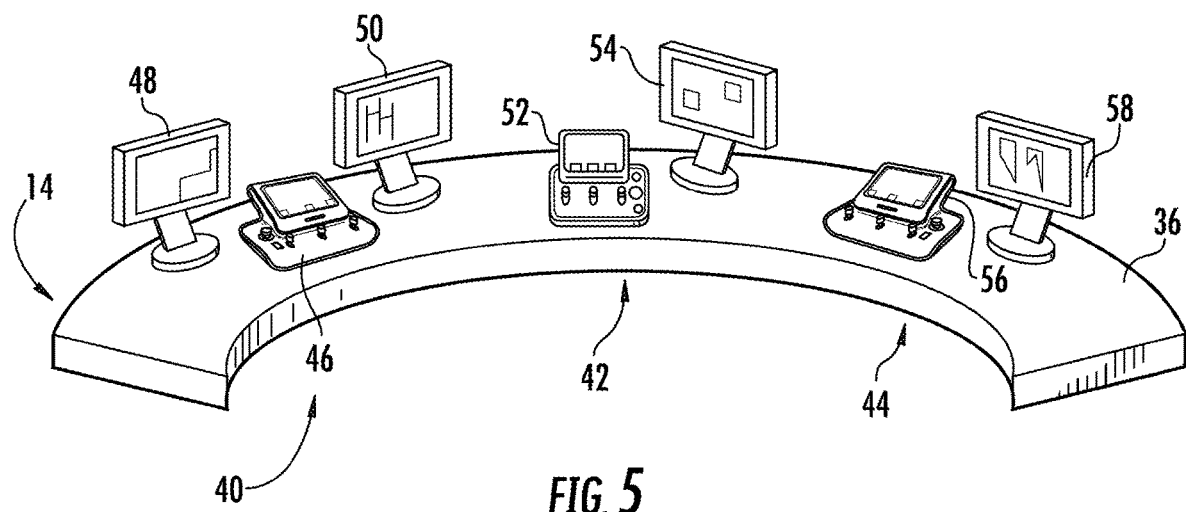
FIG. 5

REMOTE CATHETER PROCEDURE SYSTEM

CROSS-REFERENCE TO RELATED PATENT APPLICATIONS

This application is a continuation of U.S. application Ser. No. 15/372,985, filed Dec. 8, 2016, titled REMOTE CATHETER PROCEDURE SYSTEM, which is a continuation of U.S. application Ser. No. 13/152,168, filed Jun. 2, 2011, titled REMOTE CATHETER PROCEDURE SYSTEM, which is a continuation of PCT/US2009/067540, filed on Dec. 10, 2009, which claims the benefit of U.S. Provisional Application No. 61/122,263, filed Dec. 12, 2008, all of which are incorporated herein by reference in their entirety.

BACKGROUND OF THE INVENTION

The present invention relates generally to the field of catheter systems for performing diagnostic and/or therapeutic procedures. The present invention relates specifically to catheter systems including a user interface and/or workstation for controlling a robotic catheter system, an inflation device for the inflation of an angioplasty balloon and/or stent, a contrast media delivery device, and/or other related systems.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based therapeutic procedure, such as angioplasty or stent placement. Catheter based therapeutic procedures are generally considered less invasive than surgery. If a patient shows symptoms indicative of cardiovascular disease, an image of the patient's heart may be taken to aid in the diagnosis of the patient's disease and to determine an appropriate course of treatment. For certain disease types, such as atherosclerosis, the image of the patient's heart may show a lesion that is blocking one or more coronary arteries. Following the diagnostic procedure, the patient may undergo a catheter based therapeutic procedure. During one type of therapeutic procedure, a catheter is inserted into the patient's femoral artery and moved through the patient's arterial system until the catheter reaches the site of the lesion. In some procedures, the catheter is equipped with a balloon or a stent that when deployed at the site of a lesion allows for increased blood flow through the portion of the coronary artery that is affected by the lesion. In addition to cardiovascular disease, other diseases may be treated with catheterization procedures.

SUMMARY OF THE INVENTION

On embodiment of the invention relates to a catheter procedure system. The catheter procedure system includes a bedside system. The bedside system includes a catheter including an expandable percutaneous intervention device, a robotic catheter system configured to move the catheter, and an inflation device configured to cause expansion of the expandable percutaneous intervention device. The catheter procedure system also includes a remote workstation. The remote workstation includes a user interface configured to receive at least a first user input and a second user input and a control system operatively coupled to the user interface for remotely controlling both the robotic catheter system and the inflation device. The remote workstation includes a monitor configured to display information related to the expandable percutaneous intervention device. The control system controls the robotic catheter system to move the catheter based upon at least the first user input and controls the inflation device to cause expansion of the expandable percutaneous intervention device based upon at least the second user input.

Another embodiment of the invention relates to a remote workstation configured for operating both a robotic catheter system and an inflation device. The remote workstation includes a user interface configured to receive at least a first user input and a second user input. The remote workstation includes a control system to control the robotic catheter system to move at least one percutaneous device based upon at least the first user input and to control the inflation device to expand an expandable percutaneous intervention device based upon at least the second user input. The remote workstation also includes a user assistance subsystem operatively connected to the control system configured to provide information to the user to assist the user in the use of the expandable percutaneous intervention device.

Another embodiment of the invention relates to a catheter procedure system including a bedside system and a remote workstation. The bedside system includes a catheter, the catheter including an internal lumen and an expandable percutaneous intervention device. The bedside system also includes a support structure configured to be coupled to a patient bed, a robotic catheter system coupled to the support structure and configured to move the catheter, an inflation device coupled to the support structure and configured to cause expansion of the expandable percutaneous intervention device, and an inflation conduit connecting the inflation device to the internal lumen of the catheter. The remote workstation includes a monitor, controls configured to receive at least a first user input and at least a second user input, and a control system operatively coupled to the user interface for remotely controlling both the robotic catheter system and the inflation device. The control system controls the robotic catheter system to move the catheter based upon at least the first user input and controls the inflation device to cause a fluid to flow from the inflation device through the inflation conduit into the lumen of the catheter to cause expansion of the expandable percutaneous intervention device based upon at least the second user input, and the monitor displays information related to both the robotic catheter system and the inflation device.

BRIEF DESCRIPTION OF THE DRAWINGS

This application will become more fully understood from the following detailed description, taken in conjunction with the accompanying figures, wherein like reference numerals refer to like elements in which:

FIG. 5 is a perspective view of a catheter procedure system according to another exemplary embodiment;

DETAILED DESCRIPTION OF THE PREFERRED EMBODIMENTS

Figure 1:
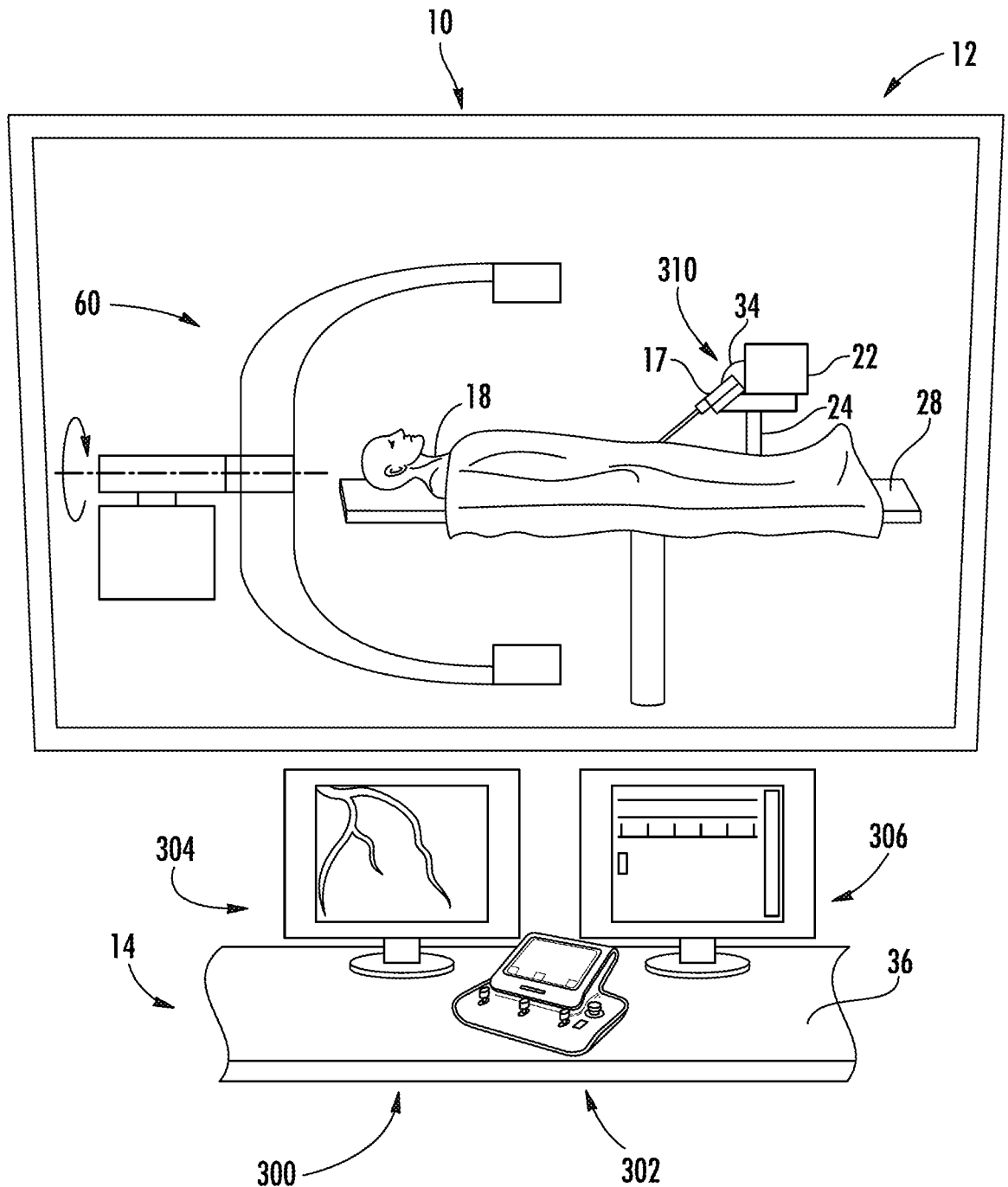
FIG. 1 is a perspective view of a catheter procedure system according to an exemplary embodiment.

Referring to FIG. 1, a catheter procedure system 10 is shown. Catheter procedure system 10 may be used to perform catheter based medical procedures (e.g., percutaneous intervention procedures). Percutaneous intervention procedures may include diagnostic catheterization procedures during which one or more catheters are used to aid in the diagnosis of a patient's disease. Percutaneous intervention procedures may also include catheter based therapeutic procedures (e.g., angioplasty, stent placement, treatment of peripheral vascular disease, etc.) during which a catheter is used to treat a disease. During both diagnostic and therapeutic procedures, images of a patient's heart may be captured using a medical imaging device. During such procedures, contrast media may be injected into the patient's vascular system to aid in image capture. It should be noted, however, that one skilled in the art would recognize that, certain specific percutaneous intervention devices or components (e.g., type of guide wire, type of catheter, etc.) will be selected based on the type of procedure that is to be preformed. Catheter procedure system 10 is capable of performing any number of catheter based medical procedures with minor adjustments to accommodate the specific percutaneous intervention devices to be used in the procedure. In particular, while the embodiments of catheter procedure system 10 described herein are explained primarily in relation to the diagnosis and/or treatment of coronary disease, catheter procedure system 10 may be used to diagnose and/or treat any type of disease or condition amenable to diagnosis and/or treatment via a catheter based procedure.

In one embodiment, catheter procedure system 10 may be equipped to perform a catheter based diagnostic procedure. In this embodiment, catheter procedure system 10 may be equipped with a variety of catheters for the delivery of contrast media to the coronary arteries. In one embodiment, catheter procedure system 10 may be equipped with a first catheter shaped to deliver contrast media to the coronary arteries on the left side of the heart, a second catheter shaped to deliver contrast media to the coronary arteries on the right side of the heart, and a third catheter shaped to deliver contrast media into the chambers of the heart.

In another embodiment, catheter procedure system 10 may be equipped to perform a catheter based therapeutic procedure. In this embodiment, catheter procedure system 10 may be equipped with a guide catheter, a guide wire, and a working catheter (e.g., a balloon catheter, a stent delivery catheter, etc.). During certain therapeutic procedures an expandable percutaneous device (e.g., an angioplasty balloon, stent, etc.) may be positioned near one end of the working catheter. The working catheter is navigated through a patient's vascular system to position the expandable percutaneous device at a portion of a blood vessel that has been narrowed due to a lesion caused by a disease, such as atherosclerosis. The expandable percutaneous device is expanded at the narrowed portion to increase the diameter of the blood vessel lumen at the lesion. This expansion allows for increased blood flow through that portion of the blood vessel. In the case of balloon angioplasty, the expandable device is an angioplasty balloon that is expanded by being inflated to compress the material of the lesion which increases the diameter of the blood vessel. In the case of stent placement, a stent is expanded and left inside the blood vessel at the site of a lesion to increase the diameter of the blood vessel. In one stent placement technique, a balloon (e.g., a balloon configured to deploy a stent) is positioned in the middle of the stent, and the expansion of the balloon expands the stent.

Catheter procedure system 10 includes a lab unit 12 and a remote workstation 14. Catheter procedure system 10 includes an integrated bedside system 310 coupled to support structure 24 located within lab unit 12 adjacent patient 18. Bedside system 310 includes a robotic catheter system 17 and an inflation device 22. Integrated bedside system 310 may include a single power supply to power both robotic catheter system 17 and an inflation device 22. In addition, integrated bedside system 310 may include a single communication link to communicably couple both robotic catheter system 17 and inflation device 22 to controller 340.

Generally, robotic catheter system 17 may be equipped with the appropriate percutaneous intervention devices or components (e.g., guide wires, guide catheters, working catheters, catheter balloons, stents, medicine, diagnostic catheters, etc.) to allow the user to perform a catheter based medical procedure. Robotic catheter system 17 may be any system configured to allow a user to interact with (e.g., move, manipulate, control, etc.) percutaneous intervention devices via a robotic system by operating various controls such as the controls located at workstation 14. Robotic catheter system 17 may include any number and/or combination of components to provide robotic catheter system 17 with the functionality described herein. One embodiment of robotic catheter system 17 is described in International Application No. PCT/US2009/042720, filed May 4, 2009, which is incorporated herein by reference in its entirety.

Inflation device 22 of bedside system 310 may be any device configured to allow a user to expand an expandable percutaneous intervention device (e.g., to inflate an angioplasty balloon or a balloon configured to deploy a stent during a therapeutic catheterization procedure). Inflation conduit 34 connects inflation device 22 to one or more expandable percutaneous devices, such as an angioplasty balloon or stent, that bedside system 310 is equipped with. In one embodiment, inflation conduit 34 is connected to an input end of a working catheter. The working catheter has an internal lumen that allows fluid to be pumped from inflation device 22 through inflation conduit 34 into the lumen of the working catheter to inflate a balloon located at the distal end of the working catheter. Inflation device 22 includes various components (e.g., pumps, valves, power supplies, inflation media reservoir, etc.) to allow a balloon to be inflated in response to the operation of controls operatively connected to inflation device 22. This balloon may be an angioplasty balloon or a stent delivery balloon. While the disclosure here relates primarily to angioplasty balloons and/or stents expanded by the expansion of a balloon, any other expandable percutaneous intervention device (e.g., shape memory alloy stents, etc.) may be used.

In one embodiment, bedside system 310 is in communication with workstation 14, allowing signals generated by user inputs located at workstation 14 to be transmitted to bedside system 310 to control the functions of robotic catheter system 17 and inflation device 22. Bedside system 310 may provide feedback signals (e.g., operating conditions, warning signals, error codes, etc.) to workstation 14. Bedside system 310 may be connected to workstation 14 via one or more communication link 38 that may be a wireless connection, cable connector, or any other means capable of allowing communication to occur between workstation 14 and the devices or systems located within lab unit 12.

In the embodiment shown in FIG. 1, workstation 14 includes a user interface 300. User interface 300 is positioned on work table 36 within workstation 14. As shown in FIG. 1, workstation 14 is a remote workstation located, for example, in either a procedure room or a separate control room. In one embodiment, a transparent protective screen or shield (e.g., leaded glass, etc.) may be positioned between workstation 14 and lab unit 12 to shield the user at workstation 14 from radiation generated within lab unit 12 (e.g., by imagining system 60). Workstation 14 may be located at any place within a hospital. Workstation 14 may also be located at any location outside of the hospital, such as in a physician's offsite office, mobile workstation trailer, etc. Lab unit 12 may include a video camera so that the user at workstation 14 is able to see patient 18 within lab unit 12 when workstation 14 is located such that direct visual inspection of lab unit 12 is not possible.

User interface 300 includes controls 302. Controls 302 allow the user to control bedside system 310 to perform a catheter based medical procedure. For example, controls 302 may be configured to cause robotic catheter system 17 to perform various tasks using the various percutaneous intervention devices with which bedside system 310 may be equipped (e.g., to advance, retract, or rotate a guide wire, advance, retract, or rotate a working catheter, advance, retract, or rotate a guide catheter, advance, retract, or rotate a diagnostic catheter, etc.). Various embodiments of user interface 300 are described in detail in International Application No. PCT/US2009/55320, filed Aug. 28, 2009, and International Application No. PCT/US2009/55318, filed Aug. 28, 2009, both of which are incorporated herein by reference in their entireties.

In addition, controls 302 allow a user to cause an angioplasty balloon or a stent placement balloon to be inflated and deflated by controlling inflation device 22. Controls 302 include one or more buttons or joysticks that allow the user located at workstation 14 to instruct inflation device 22 to inflate (e.g., expand, deploy, etc.) and/or deflate an expandable percutaneous intervention device, such as a stent or angioplasty balloon, during a percutaneous procedure. Controls 302 may be configured to allow the user to control various aspects of balloon or stent inflation and/or deflation (e.g., rate of inflation, extent of inflation, amount of time the balloon or stent remains inflated, pressure generated by inflation device 22, etc.). In one embodiment, controls 302 may include one input device (e.g., a button, knob, touch screen, etc.) that causes inflation, and a second input device (e.g., a button, knob, touch screen, etc.) to allow the user to set the rate of inflation and/or maximum inflation size or pressure. In one embodiment, operation of controls 302 activates a motor or pump of inflation device 22 to pump inflation fluid (e.g., saline solution, saline and contrast media mixture, etc.) from a fluid reservoir through inflation conduit 34 into the internal lumen of a working catheter to generate pressure that results in the expansion of an angioplasty balloon or a stent.

User interface 300 may include a first monitor 304 and a second monitor 306. First monitor 304 and a second monitor 306 may be configured to display information to the user located at workstation 14. For example, first monitor 304 and a second monitor 306 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 304 and a second monitor 306 may be configured to display other information (e.g., duration of procedure, catheter or guide wire position, volume of medicine or contrast media delivered, extent of inflation of an expandable percutaneous device, etc.). Further, monitor 304 and second monitor 306 may be configured to display information to provide the functionalities associated with the various modules of controller 340 discussed below or with the various modules disclosed in the incorporated references.

Monitors 304 and/or 306 may be configured to provide various information to the user of workstation 14 regarding an expandable percutaneous intervention device. For example, monitors 304 and/or 306 may display an image of the balloon or stent within the patient, an indication of whether bedside system 310 is currently equipped with an angioplasty balloon or a stent (e.g., a graphic represent the current device, etc.), information about the type of device being used (e.g., the size, shape, manufacturer, etc.), information about the extent of inflation of the balloon or stent, the duration of inflation, the amount of force being exerted on the balloon or stent by the vessel wall, the fluid pressure within the balloon generated by inflation system 22, etc.

Catheter procedure system 10 also includes an imaging system 60 located within lab unit 12. Imaging system 60 may be any medical imaging system that may be used in conjunction with a catheter based medical procedure (e.g., non-digital x-ray, digital x-ray, CT, MRI, ultrasound, etc.). In an exemplary embodiment, imaging system 60 is a digital x-ray imaging device that is in communication with workstation 14. As shown in FIG. 1, imaging system 60 may include a C-arm that allows imaging system 60 to partially or completely rotate around patient 18 in order to obtain images at different angular positions relative to patient 18 (e.g., sagital views, caudal views, cranio-caudal views, etc.).

Imaging system 60 is configured to take x-ray images of the appropriate area of patient 18 during a particular procedure. For example, imaging system 60 may be configured to take one or more x-ray images of the heart to diagnose a heart condition. Imaging system 60 may also be configured to take one or more x-ray images during a catheter based medical procedure (e.g., real-time images) to assist the user of workstation 14 to properly position a guide wire, catheter, angioplasty balloon, stent, etc. during the procedure. The image or images may be displayed on first monitor 304 and/or second monitor 306. In addition, the user of workstation 14 may be able to control the angular position of imaging system 60 relative to the patient to obtain and display various views of the patient's heart on first monitor 304 and/or second monitor 306. Displaying different views at different portions of the procedure may aid the user of workstation 14 to properly move and position the percutaneous intervention devices within the 3D geometry of the patient's heart. In an exemplary embodiment, imaging system 60 may be any 3D imaging modality of the past, present, or future, such as an x-ray based computed tomography (CT) imaging device, a magnetic resonance imaging device, a 3D ultrasound imaging device, etc. In this embodiment, the image of the patient's heart that is displayed during a procedure may be a 3D image. In addition, controls 302 may also be configured to allow the user positioned at workstation 14 to control various functions of imaging system 60 (e.g., image capture, magnification, collimation, c-arm positioning, etc.).

Figure 2:
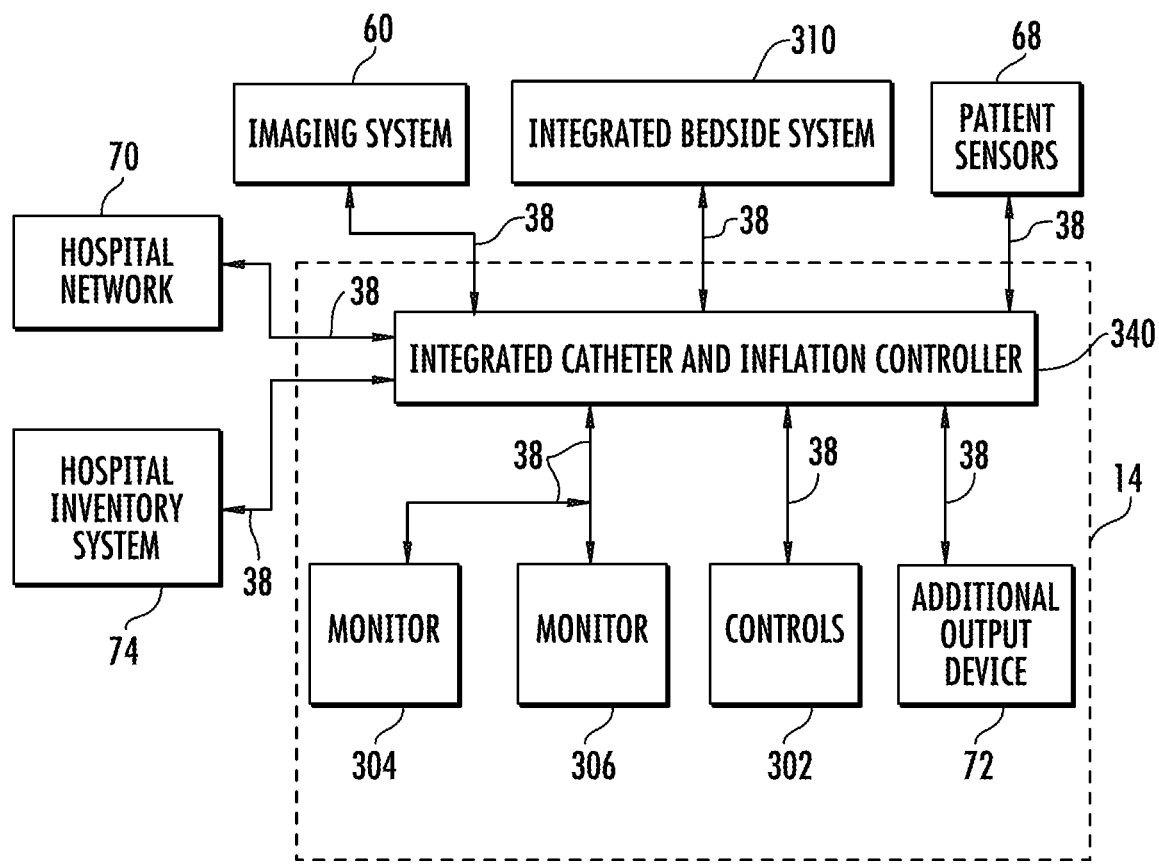
FIG. 2 is a block diagram of a catheter procedure system according to an exemplary embodiment.

Referring to FIG. 2, a block diagram of catheter procedure system 10 is shown according to an exemplary embodiment. Catheter procedure system 10 includes a control system, shown as controller 340. As shown in FIG. 2, controller 340 may be part of workstation 14. Controller 340 is in communication with one or more bedside systems 310, controls 302, monitors 304 and 306, imaging system 60, and patient sensors 68 (e.g., electrocardiogram ("ECG") devices, electroencephalogram ("EEG") devices, blood pressure monitors, temperature monitors, heart rate monitors, respiratory monitors, etc.). In addition, controller 340 may be in communication with a hospital data management system or hospital network 70, one or more additional output devices 72 (e.g., printer, disk drive, cd/dvd writer, etc.), and a hospital inventory management system 74.

Communication between the various components of catheter procedure system 10 may be accomplished via communication links 38. Communication links 38 may be dedicated wires or wireless connections. Communication links 38 may also represent communication over a network. Catheter procedure system 10 may be connected to or configured to include any other systems and/or devices not explicitly shown. For example, catheter procedure system 10 may include intravenous ultrasound systems ("IVUS systems"), image processing engines, data storage and archive systems, contrast media and/or medicine injection systems, medicine tracking and/or logging systems, user logs, encryption systems, systems to restrict access or use of catheter procedure system 10, robotic catheter systems of the past, present, or future, etc.

Figure 3:
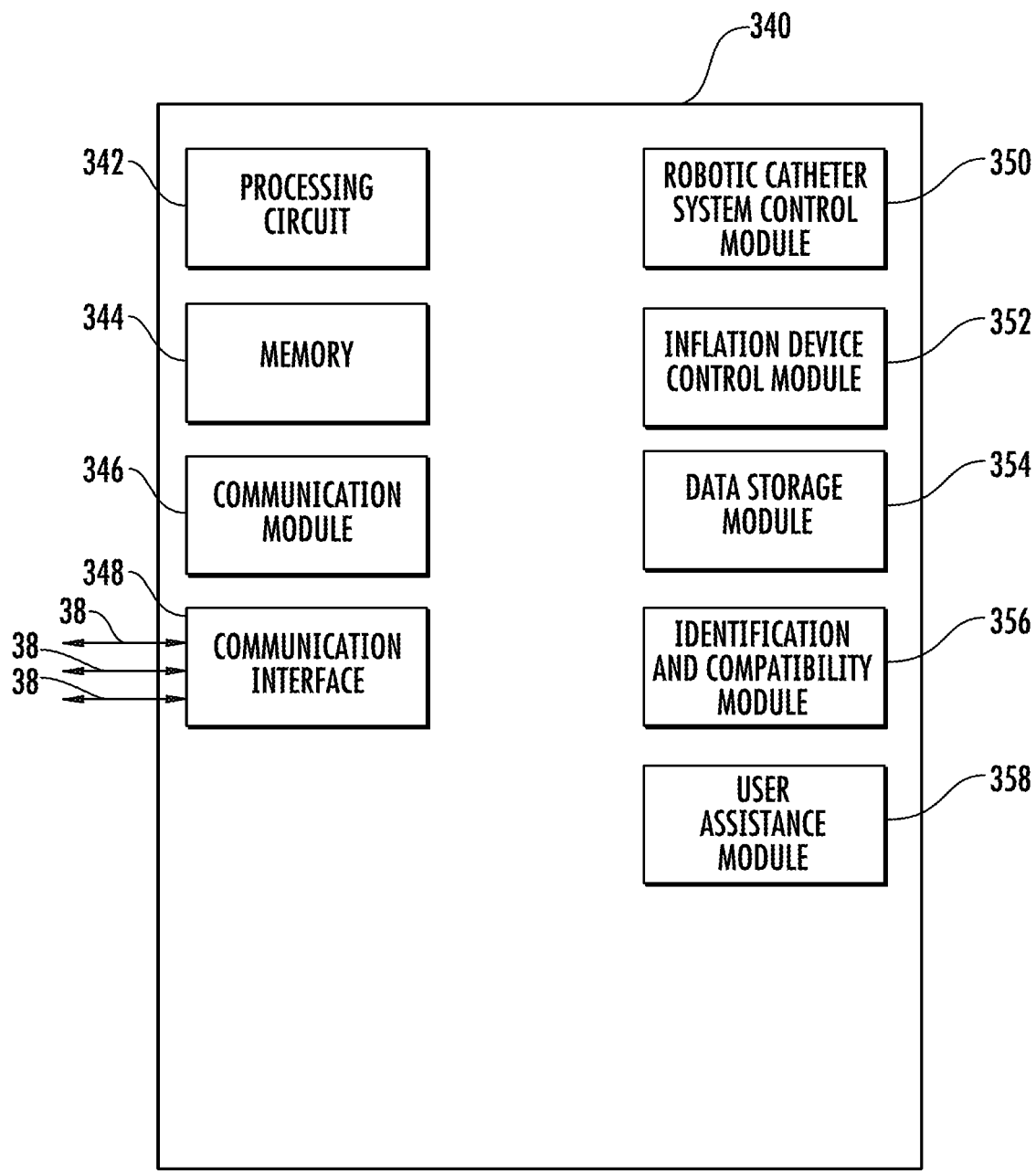
FIG. 3 is a block diagram of a control system according to an exemplary embodiment.

Referring to FIG. 3, a block diagram of controller 340 is shown according to an exemplary embodiment. Controller 340 may generally be an electronic control unit suitable to provide catheter procedure system 10 with the various functionalities described herein. For example, controller 340 may be an embedded system, dedicated circuit, general purpose system programmed with the functionality described herein, etc.

Controller 340 includes a processing circuit 342, memory 344, communication module or subsystem 346, communication interface 348, a robotic catheter system control module or subsystem 350, an inflation device control module 352, a data storage module 354, and an identification and compatibility module 356. Controller 340 may include additional modules or subsystems or combinations of modules or subsystems described herein and/or described in detail in International Application No. PCT/US2009/55320, filed Aug. 28, 2009, and International Application No. PCT/US2009/55318, filed Aug. 28, 2009, both of which are incorporated herein by reference in their entireties.

Processing circuits described herein, such as processing circuit 342, may be general purpose processors, application specific processors (ASICs), circuits containing one or more processing components, groups of distributed processing components, groups of distributed computers configured for processing, etc. configured to provide the functionality of module or subsystem components discussed herein. Memory units described herein, such as memory unit 344 (e.g., memory device, storage device, etc.), may be one or more devices for storing data and/or computer code for completing and/or facilitating the various processes described in the present disclosure. Memory units described herein may include volatile memory and/or non-volatile memory. Memory units described herein may include database components, object code components, script components, and/or any other type of information structure for supporting the various activities described in the present disclosure.

According to an exemplary embodiment, any distributed and/or local memory device of the past, present, or future may be utilized with the systems and methods of this disclosure. According to an exemplary embodiment, memory units described herein (e.g., memory unit 344) are communicably connected to one or more associated processing circuit (e.g., processing circuit 342). This connection may be via a circuit or any other wired, wireless, or network connection and includes computer code for executing one or more processes described herein. A single memory unit may include a variety of individual memory devices, chips, disks, and/or other storage structures or systems.

Module or subsystem components discussed herein may be computer code (e.g., object code, program code, compiled code, script code, executable code, or any combination thereof) for conducting each module's respective functions. Module or subsystem components discussed herein may be stored in one or more local, distributed, and/or remote memory units (e.g., memory unit 344) configured to be in communication with one or more processing circuits (e.g., processing circuit 342) or another suitable processing system.

Communication interfaces discussed herein, such as communication interface 348, include one or more component for communicably coupling the associated controller (e.g., controller 340) to the other components of catheter procedure system 10 via communication links 38. Communication interfaces may include one or more jacks or other hardware for physically coupling communication links 38 to one or more controller, an analog to digital converter, a digital to analog converter, signal processing circuitry, and/or other suitable components. Communication interfaces may include hardware configured to connect one or more controller with the other components of catheter procedure system 10 via wireless connections. Communication modules discussed herein, such as communication module 346, are configured to support the communication activities of the associated controller (e.g., negotiating connections, communication via standard or proprietary protocols, etc.).

Controller 340 includes a robotic catheter system control module 350 configured to support the control of robotic catheter system 17 during a catheter based medical procedure. Robotic catheter system control module 350 allows the manipulation of controls 302 by the user to operate robotic catheter system 17 (e.g., to advance, retract, or rotate a guide wire, advance, retract, or rotate a working catheter, advance, retract, or rotate a guide catheter, advance, retract, or rotate a diagnostic catheter, etc.). Robotic catheter system control module 350 may also cause data appropriate for a particular procedure to be displayed on monitors 304 and/or 306. Robotic catheter system control module 350 may include sets of instructions specific to various types of catheter based procedures that may be performed using robotic catheter system 17. For example, robotic catheter system control module 350 may include one set of instructions that will be executed by processing circuit 342 if robotic catheter system 17 is being used to perform a diagnostic catheterization procedure and another set of instructions that will be executed by processing circuit 342 if robotic catheter system 17 is being used to perform an therapeutic catheter procedure. In addition, controller 340 may also include a module to allow a user located at workstation 14 to operate imaging system 60 via manipulation of controls 302.

Inflation device control module 352 is configured to support the control of inflation device 22 during a catheter based medical procedure. Inflation device control module 352 allows manipulation of controls 302 by the user to operate inflation device 22 (e.g., inflation of an angioplasty balloon or stent, deflation of an angioplasty balloon or stent, etc.). Inflation device control module 352 may include separate sets of instructions to be executed for each expandable device that may be used with bedside system 310. For example, inflation device control module 352 may include one set of instructions to be executed by processing circuit 342 if bedside system 310 is equipped with an angioplasty balloon and another set of instructions to be executed by processing circuit 342 if bedside system 310 is equipped with a stent.

Controller 340 may include a user assistance module 358. In general, user assistance module 358 includes software and/or hardware configured to assist the user to perform various tasks using catheter procedure system 10. In another embodiment, user assistance module 358 may provide assistance by altering the response of inflation device 22 in response to the manipulation of controls 302 to provide for improved or optimized inflation of an expandable device (e.g., an angioplasty balloon or a stent) based on data accessible to controller 340. In other embodiments, user assistance module 358 may automate control of various components of catheter procedure system 10, such as inflation of an inflatable device. In another embodiment, user assistance module 358 may be configured to provide assistance to the user regarding the control of a fluid delivery device, such as contrast media delivery device 20, discussed below.

In one embodiment, user assistance module 358 may be configured to help prevent damage to the endothelium of the blood vessel that may be caused by the movement of the percutaneous devices within the vessel. For example, user assistance module 358 may be configured to smooth the movement of a percutaneous device (e.g., catheter, guide wire, etc.) in response to a user's manipulation of controls 302 by filtering out signals that would result in movement of the percutaneous device that is above a certain threshold. Similarly, user assistance module 358 may limit inflation of an angioplasty balloon or stent by ensuring that the rate of expansion does not exceed a maximum threshold. In these embodiments, robotic catheter system control module 350 and/or inflation device control module 352 may be configured to allow the user to toggle this protective feature on and off.

In another embodiment, user assistance module 358 is configured to automatically inflate an inflatable device at a certain rate and to a certain pressure to provide for the best clinical results. For example, user assistance module 358 may utilize image data generated by imaging system 60 to measure the size of a lesion and/or to identify the type of the lesion (e.g., a soft lesion, or a calcified lesion, etc.). This data is then used to automatically expand the inflatable device to a certain pressure at a certain rate based upon the identified characteristics of the lesion. In one embodiment, imaging system 60 includes an intravenous ultrasound system ("IVUS"), and user assistance module 358 includes a set of inflation profiles (e.g., pressure vs. time profiles, diameter vs. time profiles, etc.) to be used to treat different types of lesions. User assistance module 358 identifies which inflation profile is optimal for treatment of a particular lesion based upon the IVUS image data. In this embodiment, user assistance module 358 automatically inflates the inflatable device utilizing the inflation profile determined to be optimal to treat the particular lesion. In another embodiment, the inflation profile to be used may be selected by the user. In one embodiment, user assistance module 358 may be configured to alert (e.g., through display of an icon, audible alarm, etc.) a user that the inflatable device has been expanded to the predetermined value (e.g., size, pressure, etc.). In another embodiment, user assistance module 358 may be configured to alert (e.g., through display of an icon, audible alarm, etc.) a user that the amount of fluid (e.g., contrast media, medicine, etc.) delivered via control of a fluid delivery device, such as contrast media delivery device 20, has reached a predetermined value (e.g., volume, rate, etc.).

In another embodiment, user assistance module 358 may suggest the positioning of the inflatable device relative to the lesion to achieve better or optimal clinical results. In one embodiment, monitor 304 and/or 306 may display a real time image of the portion of the blood vessel containing the lesion. In this embodiment, user assistance module 358 may display a landmark over the real time image to indicate the optimal positioning of the inflatable device relative to the lesion as determined by user assistance module 358. The operator may align the image of the inflatable device with the landmark in the real time image to ensure proper positioning of the inflatable device.

In another embodiment, user assistance module 358 may be configured to ensure that the position of the inflatable device relative to the lesion remains substantially unchanged during the inflation procedure. In this embodiment, user assistance module 358 identifies a landmark (e.g., the desired position of the center point of the inflatable device relative to the lesion). In one embodiment, the landmark is selected by the user by identifying the landmark on the real time image of the blood vessel (e.g., by clicking on a portion of the image with a mouse, touching the portion of the image displayed on a touch-sensitive display, etc.). In another embodiment, the landmark is automatically determined by user assistance module 358. In this embodiment, user assistance module 358 may detect motion of the inflatable device relative the lesion. Detection of the relative motion may be done by analyzing the real time image of the inflatable device and the lesion and/or by positional sensors positioned in the inflatable device. If motion is detected, user assistance module 358 may automatically advance or retract the catheter equipped the inflatable device to realign a target point located along the inflatable device with the landmark of the lesion. Inflation of the inflatable device is allowed to proceed following the realignment of the inflatable device with the landmark. In another embodiment, user assistance module 358 may alter (e.g., decrease rate of expansion, increase rate of expansion, etc.) the expansion of the inflatable device based upon the position of the one of the other percutaneous devices (e.g., guide wire, guide catheter, etc.) in order to synchronize the expansion of the inflatable device with movement of one of the other percutaneous devices. In another embodiment, the user assistance module 358 of the control system is configured to cause or trigger expansion of the inflatable device when the target point is aligned with the landmark and to prevent, slow, or stop expansion of the inflatable device when the target point of the inflatable device is not aligned with the landmark.

In another embodiment, user assistance module 358 may delay and/or accelerate the inflation of an inflatable device based on data related to the state of heart contraction (e.g., based on whether the heart is undergoing systole or diastole). This data may be obtained from electrocardiogram data generated by patient sensors 68, from image data, or from any other information source. In one embodiment, if the user manipulates controls 302 to trigger inflation of the inflatable device during systole, user assistance module 358 will delay the inflation of balloon or stent so that the balloon or stent actually inflates during diastole. In another embodiment, user assistance module 358 may be configured to alter the delivery of a fluid, such as contrast media, caused by operation of a fluid delivery device, such as contrast media delivery device 20, such that the fluid is delivered during the systolic phase of the patient's heart. In one embodiment, user assistance module 258 may delay and/or accelerate delivery of the fluid in response to a user input to ensure that the fluid is delivered during the desired stage of heart contraction.

In another embodiment, user assistance module 358 may be configured to provide suggestions to the user that are displayed on monitors 304 and/or 306 regarding the performance of various steps of the procedure. For example, user assistance module 358 may suggest the pressure to be used to inflate a particular inflatable device based upon various information (e.g., the particular lesion being treated, the geometry of particular patient's vessel, etc.). User assistance module 358 may suggest an inflation rate to be used to inflate a particular inflatable device based upon various information (e.g., the particular lesion being treated, the geometry of particular patient's vessel, etc.). This embodiment allows the user to decide whether to follow the suggestion generated by user assistance module 358 or to preform the procedure in another way.

In another embodiment, user assistance module 358 may improve, optimize, or automate the control of imaging system 60. In one embodiment, controller 340 automatically alters the angular position of the imaging system 60 relative to the patient to obtain an image of the lesion. In another embodiment, contrast media is injected, images of the lesion are taken, and the inflatable device is inflated based on the state of contraction of the patient's heart. In another embodiment, images of the inflation procedure are taken timed to various steps of the procedure. This may reduce the radiation dose and amount of contrast media used by only taking images during the most relevant portions of the inflation procedure as contrasted with constantly imaging the patient during the whole procedure. For example, user assistance module 358 may be configured to automatically image the area of the lesion and the inflatable device when the device is at one percent inflation, fifty percent inflation, and one hundred percent inflation. In another embodiment, user assistance module 358 may be configured to alter (e.g., delay, or accelerate) control, in response to a user input, of a fluid delivery device, such as contrast media delivery device 20, based upon the movement of the at least one percutaneous device in order to synchronize the delivery of the fluid with the movement of the percutaneous device. For example, contrast media may be delivered immediately prior to movement of a percutaneous device to ensure an image of taken during movement of the percutaneous device has maximum resolution. In one embodiment, delivery of the contrast agent may be in response to the user input indicating movement of the percutaneous device to ensure the movement of the device is accompanied by a new injection of contrast media.

In another embodiment, user assistance module 358 is configured to provide suggestions or recommendations regarding the particular type (e.g., compliant angioplasty balloon, noncompliant angioplasty balloon, stent, etc.), make, model, size, etc., of inflatable device to be used for a particular procedure. The suggestion may be based upon the size, geometry, and type of lesion, and/or the size and geometry of the blood vessel. This information may be derived from image data of the lesion obtained during a diagnostic catheterization procedure or any other imaging procedure. In other embodiments, the suggestion regarding the type of inflatable device may factor in the personal preferences of a user, and/or may be based in part on the performance of a simulated therapeutic procedure.

As discussed above, controller 340 may be in communication with hospital inventory system 74. In one embodiment, the suggestion regarding the type of inflatable device made by user assistance module 358 may be based upon whether particular devices are available in the hospital's inventory at the time of the procedure. In another embodiment, user assistance module 358 may be configured to automatically order the suggested inflatable device so that the suggested inflatable device is available to the user at the time of the procedure.

Inflation device control module 352 may also cause data appropriate for a particular procedure to be displayed on monitors 304 and/or 306 during a procedure. In one embodiment, inflation device control module 352 is configured to cause the display of information related to the state of inflation of the angioplasty balloon or stent caused by the inflation device 22. In one embodiment, the display is a digital or analog gauge displaying the pressure generated by inflation device 22. This display may show pressure in any unit of pressure measurement (e.g., atmospheres, pascal, pounds per square inch, bar, etc.). In another embodiment, the display may show an image of the angioplasty balloon or stent at various stages of expansion.

In another embodiment, inflation device control module 352 may cause various information regarding the angioplasty balloon or stent that is being used to display on monitors 304 and/or 306. Information displayed may include information regarding the make, model, size, suggested uses, recommended operating conditions, etc. for angioplasty balloons or stents that may be used with bedside system 310. In one embodiment, the display may show the manufacturer's recommended maximum inflation pressure to be used with a particular inflatable device. For non-compliant balloons the display may indicate the size of the balloon following inflation. For compliant balloons, the display may indicate the size of the balloon for various pressures. In another embodiment, the display may provide a graph (e.g., a bar graph, a pie graph, etc.) showing the current pressure supplied by inflation device 22 related to the maximum pressure needed to achieve a certain level of inflation.

In certain embodiments, one or more component of catheter procedure system 10 (e.g., controller 340) has access to information regarding the particular type of angioplasty balloon or stent being used to perform the current procedure. Controller 340 may identify the particular type of inflatable device (e.g., angioplasty balloon or stent) being used in a variety of ways. In one embodiment, the user selects the particular type of inflatable device being used by interacting with a graphical user interface displayed on monitors 304 and/or 306. In one embodiment, the user may select the type of inflatable device used from a drop down menu. In other embodiments, a bar code on the inflatable device is read to allow controller 340 to identify the inflatable device. In another embodiment, a radio frequency ID tag associated with the inflatable device is read.

As shown in FIG. 3, controller 340 may also include a data storage module 354. Data storage modules discussed herein, such as data storage module 354, are configured to support the storage and retrieval of information by the associated controller, such as controller 340. In one embodiment, a data storage module may be a database for storing patient data, including image data. In another embodiment, a data storage module may be located on hospital network 70. Data storage modules and/or communication modules described herein may also be configured to import and/or export patient data from hospital network 70 for use by one or more of the controllers discussed herein. In one embodiment, controller 340 includes an identification and compatibility module 356. As discussed in more detail below, identification and compatibility module 356 may be configured to allow controller 340 to identify and control different types (e.g., makes, models, versions, etc.) of devices and/or systems, such as bedside system 310, that may be communicably coupled to controller 340.

Figure 4A:
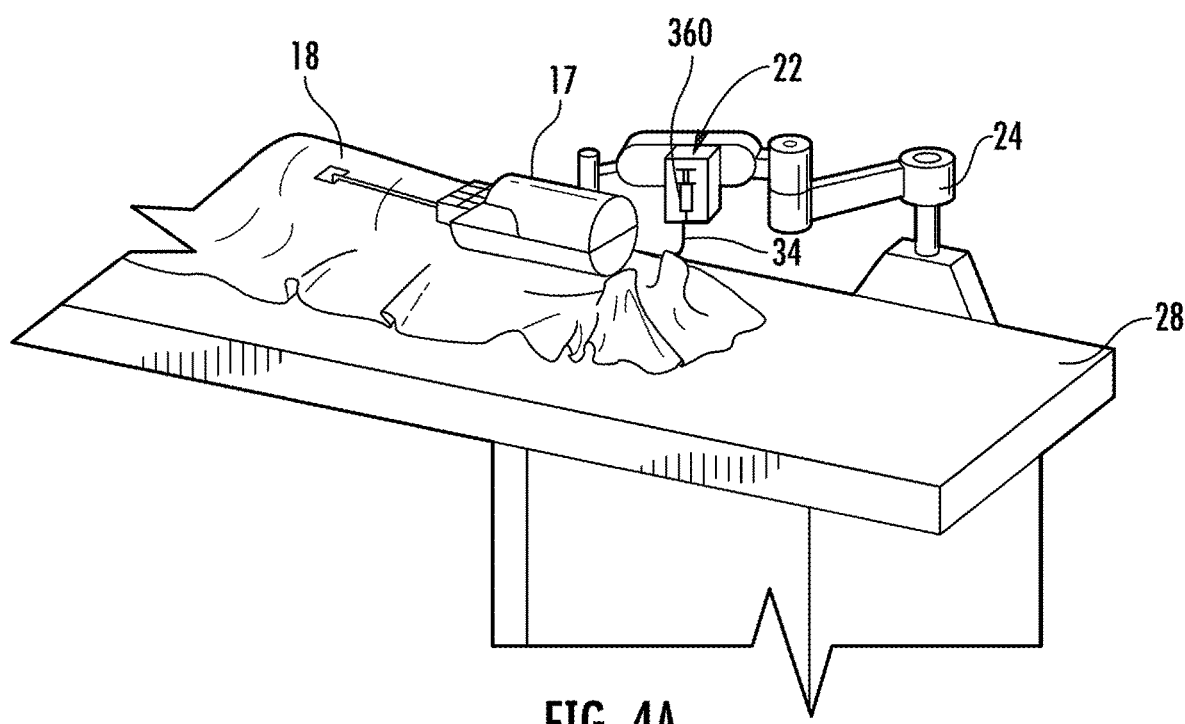
FIG. 4A is a perspective view of a bedside system according to an exemplary embodiment.
Figure 4B:
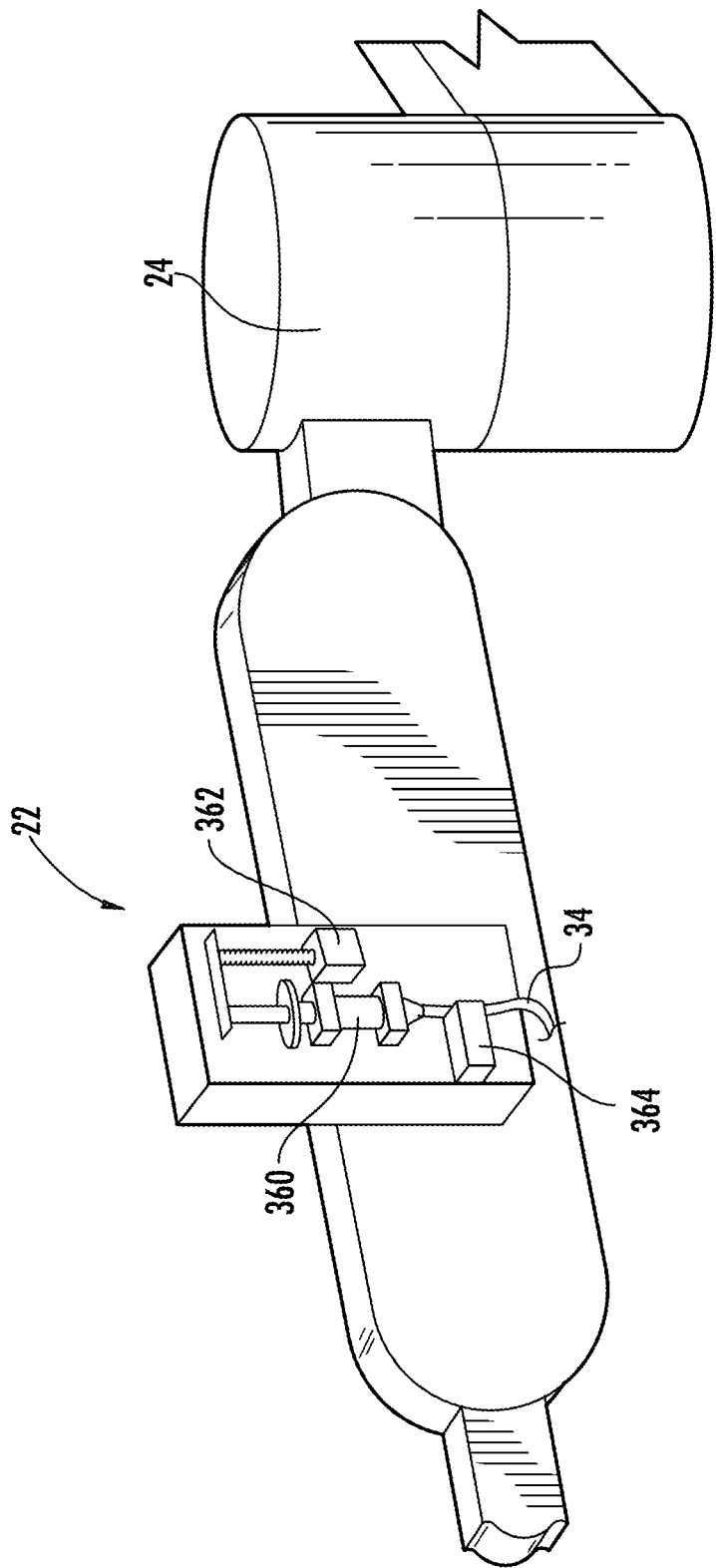
FIG. 4B is a close up view of a bedside system according to an exemplary embodiment.

FIGS. 4A and 4B show bedside system 310, including a robotic catheter system 17 integrated with inflation device 22 according to an exemplary embodiment. As shown in FIG. 4A, support structure 24 may include a series of articulating segments attached to and supported by patient bed 28. Inflation device 22 includes a pump, shown as plunger 360, and a pump drive, shown as motor 362. The output of plunger 360 is connected to inflation conduit 34 that connects plunger 360 to the internal lumen of the working catheter equipped with the inflatable device.

In operation, plunger 360 is filled with an inflation fluid (e.g., saline solution, saline/contrast media solution, etc.). Motor 362 responds to the manipulation of controls 302 to force fluid from plunger 360, through inflation conduit 34 into the internal lumen of the working catheter to inflate an inflatable balloon located at the distal end of the working catheter. Inflation device 22 includes a pressure sensor, such as pressure transducer 364, located at the output end of plunger 360. Pressure transducer 364 reads the pressure generated by plunger 360. This information may be communicated via a communication link 38 to controller 340.

In one embodiment, catheter procedure system 10 may include additional controls configured to control inflation device 22 located within lab unit 12. This may allow a user located within lab unit 12 to control inflation device 22 during a manually performed percutaneous catheter procedure (i.e., a procedure in which robotic catheter system 17 is not being operated via controls at remote workstation 14 to move the guide wire, guide catheter, working catheter, etc.). In one embodiment, the portion of controls 302 configured to control inflation device 22 may include a wireless device allowing the user to carry the inflation device controls into lab unit 12 to control inflation device 22 from within lab unit 12 during a manually performed percutaneous catheter procedure.

In another embodiment, bedside system 310 may include a connector or adaptor to connect bedside system 310 to a stand alone inflation device. In this embodiment, the inflation device integrated in bedside system 310 may be disabled while the stand alone inflation device is connected to bedside system 310. In this embodiment, the stand alone inflation device may be controlled by controls associated with the stand alone inflation device. However, in another embodiment, integrated controller 340 may include software and/or hardware sufficient to allow the user to control the stand alone inflation device via manipulation of controls 302 instead of controlling the integrated inflation device 22.

Referring to FIGS. 5-9, in another embodiment, catheter procedure system 10 may include separate (i.e., non-integrated) devices for performing catheter based procedures remotely from workstation 14. In this modular embodiment, various components of catheter procedure system 10 may be configured to be easily interchangeable and compatible with components of various makes and models. In this embodiment, lab unit 12 includes a non-integrated bedside system 16. In the embodiment of FIG. 5, non-integrated bedside system 16 includes a stand alone robotic catheter system 17, a stand alone fluid delivery device, shown as contrast media delivery device 20, and a stand alone inflation device 22. Robotic catheter system 17, contrast media delivery device 20, and inflation device 22, are each positioned near patient 18 on separate support structures 24, 26, and 32 attached to patient bed 28. In other embodiments, each support structure 24, 26, and 32 may be a separate structure, such as a cart or table located near patient 18.

A fluid delivery device, such as contrast media delivery device 20, may be any device configured to allow a user to administer contrast media to patient 18 during a percutaneous intervention procedure. In other embodiments, a fluid delivery device may be any device configured to allow a user to administer a fluid (e.g., medicine, saline, etc.) to patient 18 during a percutaneous intervention procedure. For example, the fluid delivery device may be a medication delivery device configured deliver medicine to a patient. Contrast media conduit 30 connects contrast media delivery device 20 to one or more of the percutaneous devices, such as a guide catheter or diagnostic catheter, that bedside system 16 is equipped with. Contrast media delivery device 20 includes various components (e.g., pumps, valves, power supplies, contrast media reservoirs, etc.) to allow contrast media to be administered to the patient in response to the operation of controls operatively connected to contrast media delivery device 20.

In one embodiment, robotic catheter system includes a "Y-connector" which is in fluid communication with the lumen of a guide catheter or diagnostic catheter. In this embodiment, an output end of contrast media conduit 30 is connected to the input end of the "Y-connector." When the user operates the controls associated with contrast media delivery device 20, contrast media delivery device 20 pumps contrast media from the contrast media reservoir through contrast media conduit 30 through the "Y-connector" into the lumen of the guide or diagnostic catheter. The contrast media then travels through the lumen of the guide or diagnostic catheter to exit the distal end of the catheter into the desired position of the patient's vascular system. Contrast media is delivered to the portion of the patient's vascular system to be imaged to provide increased contrast between the lumen of the blood vessel and the other structures such as the blood vessel wall or lesions within the vessel. In an embodiment including a medicine delivery device, a conduit may connect the medicine delivery device to the lumen of the guide or diagnostic catheter. While not shown, contrast media delivery device 20 may be used with the catheter procedure system shown in FIGS. 1-4.

Catheter procedure system 10 also includes a stand alone inflation device 22 coupled to a support structure 32. Inflation device 22 may be any device configured to allow a user to inflate an angioplasty balloon or stent during a therapeutic catheterization procedure. As discussed above, an inflation conduit 34 connects inflation device 22 to one or more expandable percutaneous devices, such as an angioplasty balloon or stent, that bedside system 16 is equipped with. Inflation device 22 includes various components (e.g., pumps, valves, power supplies, inflation media reservoir, etc.) to allow a stent or angioplasty balloon to be inflated in response to the operation of controls operatively connected to inflation device 22.

In one embodiment, lab unit 12 includes one or more device to aid in the positioning and organization of devices within the lab unit 12. In one embodiment, robotic catheter system 17, contrast media delivery device 20, and inflation device 22 are powered by a common power supply located within lab unit 12. In another embodiment, robotic catheter system 17, contrast media delivery device 20, and inflation device 22 are positioned on a common cart with wheels that permits the components of bedside system 16 to be moved within lab unit 12.

Similar to the embodiment of FIGS. 1-4, the components of bedside system 16 (e.g., robotic catheter system 17, contrast media delivery device 20, and inflation device 22) are in communication with a remote workstation 14, allowing signals generated by user inputs located at workstation 14 to be transmitted to the various components of bedside system 16. Bedside system 16 may provide feedback signals (e.g., operating conditions, warning signals, error codes, etc.) to workstation 14. Bedside system 16 may be connected to workstation 14 via one or more communication link 38 that may be a wireless connection, cable connectors, or any other means capable of allowing communication to occur between workstation 14 and the devices or systems located within lab unit 12.

In the embodiment shown in FIG. 5, workstation 14 includes a dedicated robotic catheter system user interface 40, a dedicated contrast media user interface 42, and a dedicated inflation interface 44. Robotic catheter system user interface 40, contrast media user interface 42, and inflation interface 44 are positioned on work table 36 within workstation 14. In one embodiment, work table 36 is curved to allow the user to easily move between robotic catheter system user interface 40, contrast media user interface 42, and inflation interface 44. In another embodiment, work table 36 comprises two or more tables positioned at an angle relative to each other. In another embodiment, work table 36 is a straight rectangular table. In another embodiment, each user interface may be positioned on a movable and/or adjustable work table 36 to allow the user to position each user interface to suit the user's personal preference. For example, work table 36 may comprise one or more wheeled carts, adjustable height tables, adjustable position tables, etc. In another embodiment, workstation 14 includes a common power supply to power dedicated robotic catheter system user interface 40, dedicated contrast media user interface 42, and dedicated inflation interface 44.

Robotic catheter system user interface 40 includes controls 46. Controls 46 allow the user to control robotic catheter system 17 to perform a catheter based medical procedure. For example, controls 46 may be configured to cause robotic catheter system 17 to perform various tasks using the various percutaneous intervention devices with which bedside system 16 may be equipped (e.g., to advance, retract, or rotate a guide wire, advance, retract, or rotate a working catheter, advance, retract, or rotate a guide catheter, advance, retract, or rotate a diagnostic catheter, etc.). Robotic catheter system user interface 40 may also include a first monitor 48 and second monitor 50 to display information as discussed above regarding monitors 304 and 306.

Contrast media user interface 42 includes contrast media controls 52 and contrast media display 54. Contrast media controls 52 include one or more buttons or joysticks that allow the user located at workstation 14 to instruct contrast media delivery device 20 to deliver contrast media to patient 18 during a percutaneous procedure. Contrast media controls 52 may be configured to allow the user to control various aspects of contrast media delivery (e.g., speed or rate of delivery, amount of contrast media delivered, timing of delivery, etc.). Contrast media display 54 is configured to provide various information to the user regarding the delivery of contrast media to patient 18. For example, contrast media display 54 may display the amount of contrast media delivered during the current procedure, the type of contrast media being delivered, the current rate of delivery, the amount of contrast media left in the reservoir of contrast media delivery device 20, etc. In one embodiment, the amount of contrast media delivered during a specified time period is displayed. This time period may be a set number of minutes, hours, days, or weeks, etc. The appropriate time period may depend on the particular type of contrast media used and on the particular patient. In one embodiment, a user assistance module or subsystem, such as user assistance module 358, may be configured to alert the user when the amount of contrast agent delivered reaches a certain predetermined value (e.g., a maximum amount for the specified period of time, etc.).

Inflation interface 44 includes inflation controls 56 and inflation display 58. Inflation controls 56 include one or more buttons or joysticks that allow the user located at workstation 14 to instruct inflation device 22 to inflate (e.g., expand, deploy, etc.) and/or deflate an inflatable percutaneous intervention device, such as a stent or angioplasty balloon, during a percutaneous procedure. Inflation controls 52 may be configured to allow the user to control various aspects of balloon or stent inflation and/or deflation (e.g., rate of inflation, extent of inflation, amount of time the balloon or stent remains inflated, etc.). Inflation display 58 is configured to provide various information to the user of workstation 14 regarding the state of an expandable percutaneous intervention device. For example, inflation display 58 may display an image of the balloon or stent within the patient, an indication of whether bedside system 16 is currently equipped with an angioplasty balloon or a stent, information about the type of device being used (e.g., the size, shape, manufacturer, etc.), information about the extent of inflation of the balloon or stent, the duration of inflation, the amount of force being exerted on the balloon or stent by the vessel wall, etc. Catheter procedure system 10 may also include an imaging system 60 as discussed above.

Figure 6:
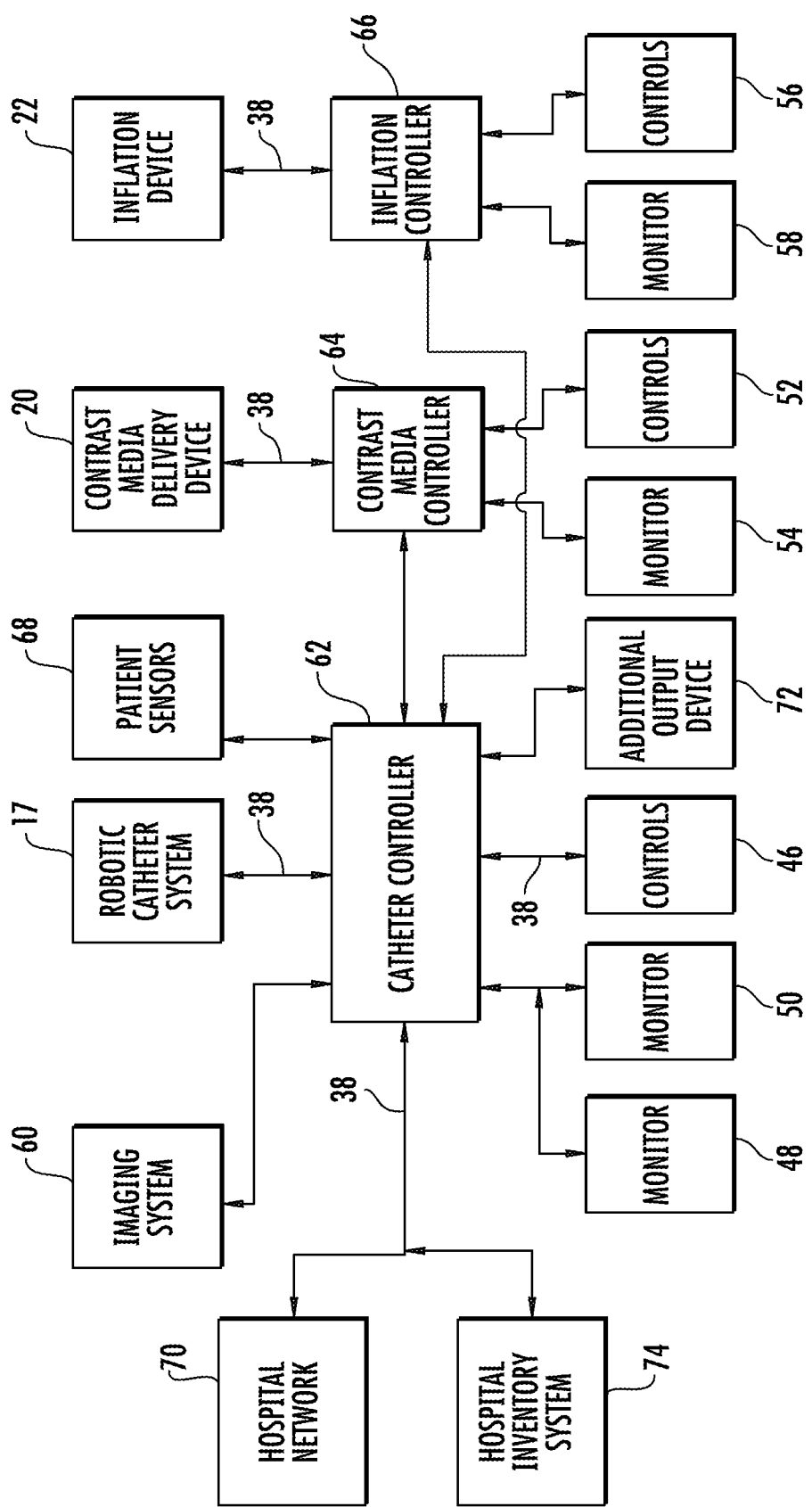
FIG. 6 is a block diagram of the catheter procedure system shown in FIG. 5 according to an exemplary embodiment.

Referring to FIG. 6, a block diagram of catheter procedure system 10 is shown according to an exemplary embodiment. In this embodiment, each stand alone component of bedside system 16 directly communicates with a dedicated control system. For example, catheter procedure system 10 may include a first control system, shown as catheter controller 62. Controller 62 is in communication with one or more robotic catheter systems 17, catheter controls 46, monitors 48 and 50, imaging system 60, and patient sensors 68. In addition, controller 62 may be in communication with a hospital data management system or hospital network 70, one or more additional output devices 72 (e.g., printer, disk drive, cd/dvd writer, etc.), and a hospital inventory management system 74.

In addition, catheter procedure system 10 includes a second control system, shown as contrast media controller 64 and a third control system, shown as inflation controller 66. Contrast media controller 64 is in communication with one or more contrast media delivery devices 20, contrast media display 54, and contrast media controls 52. Inflation controller 66 is in communication with inflation device 22, inflation display 58, and inflation controls 56. In one embodiment, controllers 62, 64, and 66 may also be communicably coupled to each other allowing for the transfer of information between each of the dedicated controllers 62, 64, and 66. As discussed above, communication between the various components of catheter procedure system 10 may be accomplished via communication links 38.

Figure 7:
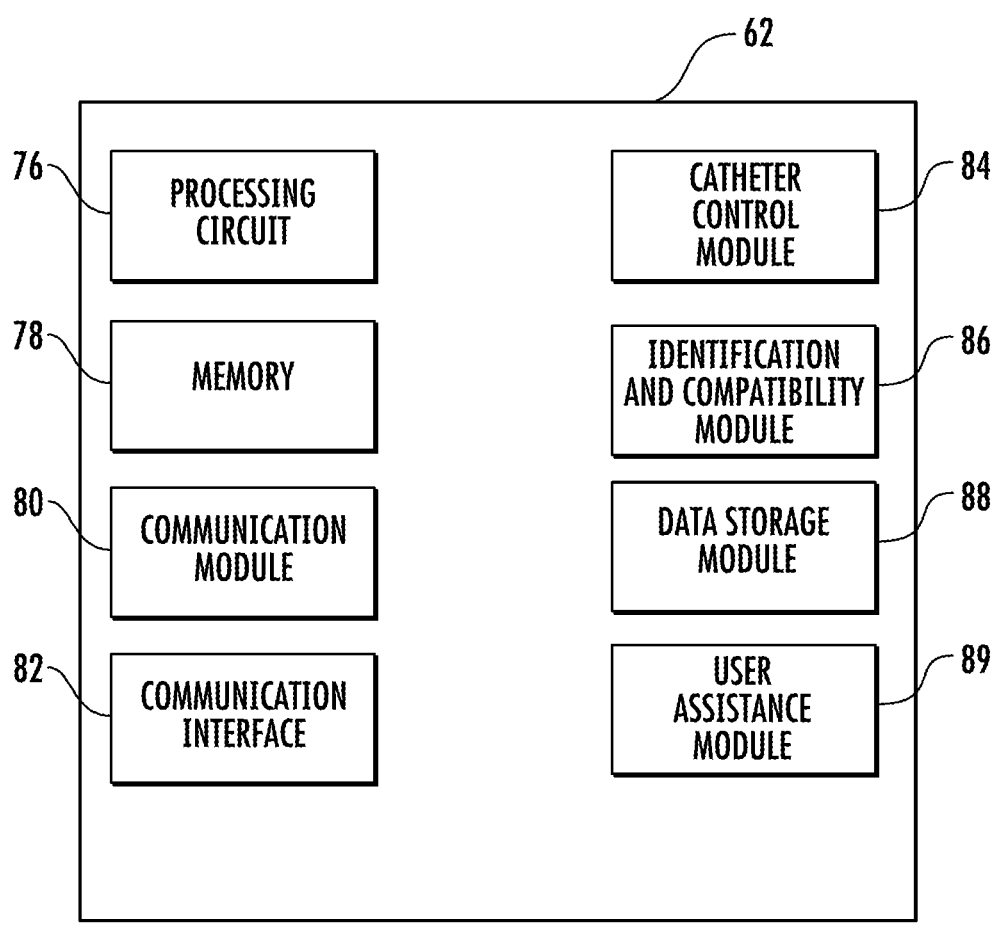
FIG. 7 is a block diagram of a catheter control system according to an exemplary embodiment.
Figure 8:
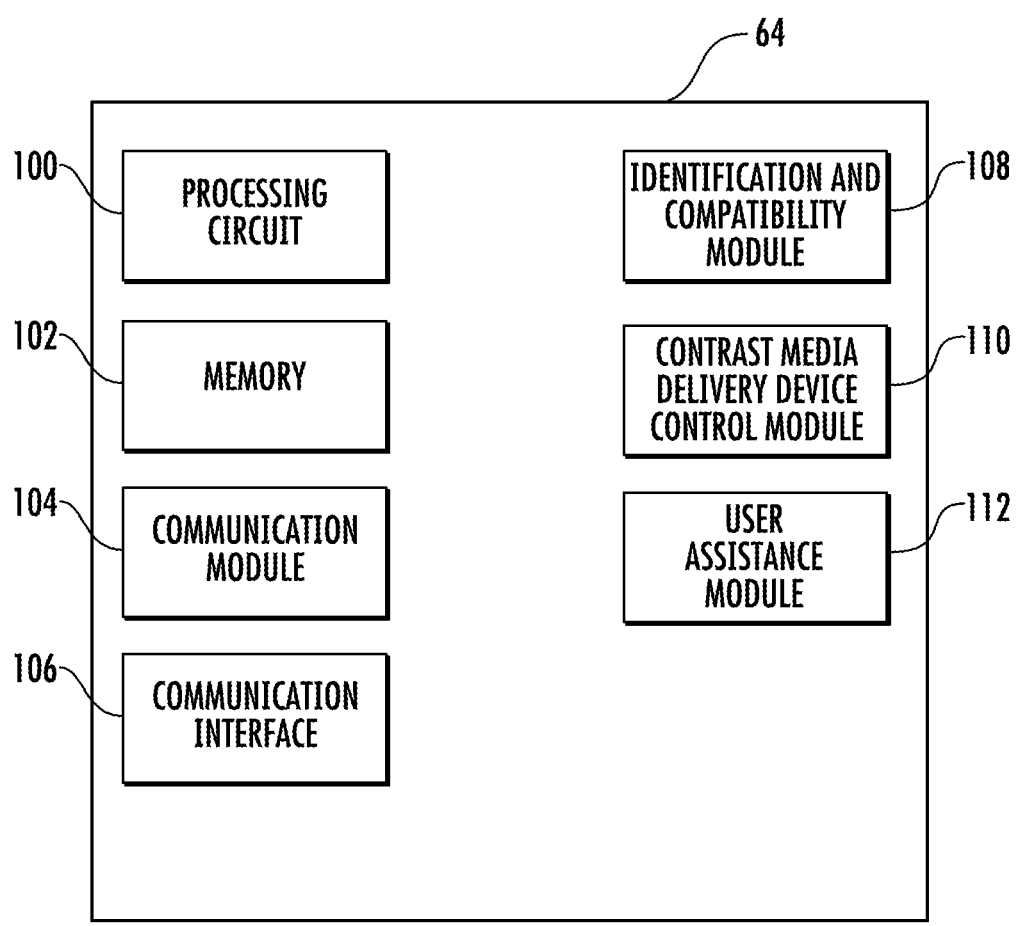
FIG. 8 is a block diagram of a contrast media delivery device control system according to an exemplary embodiment.
Figure 9:
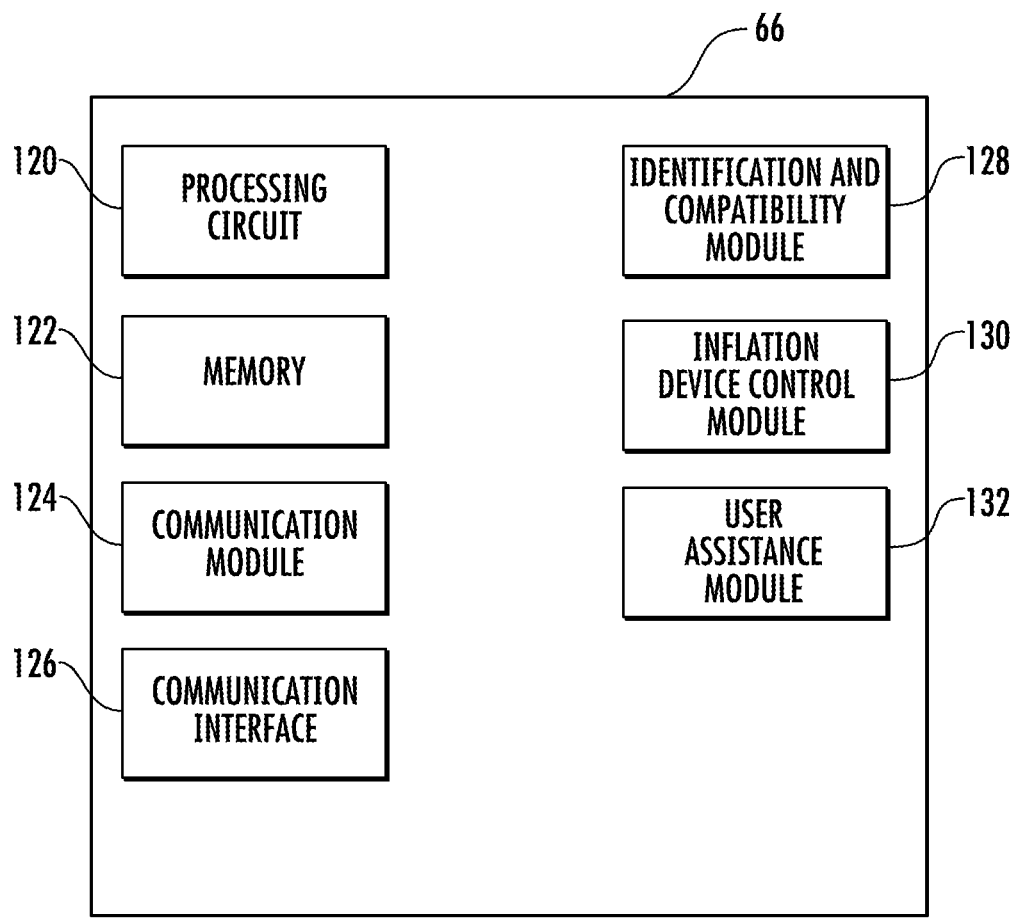
FIG. 9 is a block diagram of an inflation device control system according to an exemplary embodiment.

Referring to FIGS. 7-9, block diagrams of controller 62, controller 64, and controller 66 are shown according to exemplary embodiments. Controllers 62, 64, and 66 may generally be an electronic control unit suitable to provide catheter procedure system 10 with the various functionalities described herein. For example, controllers 62, 64, and 66 may be embedded systems, dedicated circuits, general purpose systems programmed with the functionality described herein, etc.

Controller 62 includes a processing circuit 76, memory 78, communication module or subsystem 80, communication interface 82, catheter system control module or subsystem 84, a compatibility module 86, a data storage module 88, and a user assistance module 89. Controller 62 may include additional modules or subsystems such as those described in described in detail in International Application No. PCT/US2009/55320, filed Aug. 28, 2009, and International Application No. PCT/US2009/55318, filed Aug. 28, 2009, both of which are incorporated herein by reference in their entireties. Referring to FIG. 8, contrast media controller 64 includes a process circuit 100, memory 102, communication module 104, communication interface 106, compatibility module or subsystem 108, contrast media delivery device control module or subsystem 110, and a user assistance module or subsystem 112. Referring to FIG. 9, inflation controller 66 includes a process circuit 120, memory 122, communication module 124, communication interface 126, compatibility module or subsystem 128, inflation device control module or subsystem 130, and a user assistance module or subsystem 132.

Similar to catheter system control module 350, catheter system control module 84 is configured to support the control of robotic catheter system 17 during a catheter based medical procedure. Catheter system control module 84 allows the manipulation of catheter controls 46 by the user to operate robotic catheter system 17. Catheter system control module 84 may also cause data appropriate for a particular procedure to be displayed on monitors 48 and 50. In addition, procedure control module 84 may also be configured to allow a user located at workstation 14 to operate imaging system 60.

Contrast media controller 64 includes a contrast media delivery device control module 110 configured to support the control of contrast media delivery device 20 during a catheter based medical procedure. Contrast media delivery device control module 110 allows manipulation of controls 52 by the user to operate contrast media delivery device 20. Contrast media delivery device control module 110 may also cause data appropriate for a particular procedure to be displayed on monitor 54 during a procedure.

Inflation controller 66 includes an inflation device control module 130 configured to support the control of inflation device 22 during a catheter based medical procedure. Similar to inflation device control module 352, inflation device control module 130 allows manipulation of controls 56 by the user to operate inflation device 22. Inflation device control module 130 may also cause data appropriate for a particular procedure to be displayed on monitor 58 during a procedure.

FIGS. 5-9 illustrate a modular embodiment of catheter procedure system 10. In this embodiment, catheter controller 62 may be connected to controllers 64 and 66 via communication links 38 to facilitate communication and exchange of data between the controllers 62, 64, and 66. In this embodiment, data accessible to procedure controller 62 (e.g., patient information archived on hospital network 70, data from patient sensors 68, data from imaging system 60, positional information of percutaneous devices, etc.) may be shared with contrast media controller 64 and/or inflation controller 66. This data may then be processed or displayed by controllers 64 and/or 66. In addition, data accessible to contrast media controller 64 (e.g., flow rate of contrast media, amount of contrast media delivered, etc.) and/or data accessible to inflation controller 66 (e.g., extent of stent/balloon inflation, rate of stent/balloon inflation, etc.) may be shared with catheter controller 62. This data may then be processed or displayed by controller 62. For example, data transferred from contrast media controller 64 and/or inflation controller 66 may be displayed on monitor 48 and/or monitor 50 associated with controller 62 instead of or in addition to display of this information on monitors 54 and 58. In this embodiment, controller 62 may be configured to provide a standardized visual display of information related to each of robotic catheter system 17, contrast media delivery device 20, and/or inflation device 22.

In one embodiment, catheter controller 62 is configured to act as a server or host to one or more controllers 64 and 66 in a server/client relationship. In another embodiment, procedure controller 62 includes a data storage module 88 that is configured to support the storage and retrieval of information by controller 62. In one embodiment, data storage module 88 is a database for storing patient data, including image data. In another embodiment, data storage module 88 may be located on hospital network 70. Data storage module 88 and/or communication module 80 may also be configured to import and/or export patient data from hospital network 70 for use by controller 62. Communication links 38 between controllers 62, 64, and 66 may allow data stored by data storage module 88 to be transferred or accessed by controllers 64 and 66. In addition, data transferred to controller 62 from controllers 64 and 66 may be stored within data storage module 88.

In this embodiment, the data from controllers 62, 64, and 66 may be associated with a particular file or record for a particular patient. In one embodiment, data from controllers 62, 64, and 66 may be aggregated to generate a combined report to show the operation of each of the stand alone components of bedside system 16 during a particular procedure. For example, the combined report may show graphs representing the movement of the guide wire, guide catheter, and working catheter at various time points during the procedure. This graph may also show operation of contrast media delivery device 20 and inflation device 22 at these same times. In one embodiment, a single graph may be generated showing the amount of contrast media delivered vs. time, the fluid pressure generated by inflation device 22 vs. time, and the movement of a percutaneous device vs. time.

In another embodiment, controller 62 may be linked directly to contrast media delivery device 20 and/or inflation device 22 via one or more communication links 38 instead of or in addition to being connected to controllers 64 and 66. In this case, information related to contrast media delivery device 20 (e.g., flow rate of contrast media, amount of contrast media delivered, etc.) and/or inflation device 22 (e.g., extent of stent/balloon inflation, rate of stent/balloon inflation, etc.) may be communicated directly to controller 62. In this case, the data may be stored, processed, displayed, etc. as discussed herein.

Further, in the modular embodiment, communication links 38 between procedure controller 62, media controller 64, and/or inflation controller 66 are configured to be easy to establish and to disconnect to allow for convenient removal/addition of the various modular components. For example, procedure controller 62 may be compatible with many different types (e.g., versions, makes, models, etc.) of contrast media controllers 64 and/or inflation controllers 66. In this case, the communication interfaces of controllers 62, 64, and 66 include easily accessible ports or jacks to allow the user to easily attach the appropriate cables between controllers 62, 64, and 66 to act as communication links 38 between these devices. In another embodiment, the communication modules and/or communication interfaces may include software and/or hardware to facilitate the convenient establishment of wireless communication links between controllers 62, 64, and 66. In other embodiments, the communication interfaces associated with controllers 62, 64, and 66 may be standard communication interfaces (e.g., USB, firewire, Bluetooth, etc.). In other embodiments, the communication interfaces associated with controllers 62, 64, and 66 may be proprietary.

In addition, catheter controller 62 may include an identification and compatibility module 86. Compatibility module 86 allows catheter controller 62 to identify the particular contrast media controller 64 and/or inflation controller 66 to which catheter controller 62 has been connected. Following identification, compatibility module 86 activates the proper software, hardware, drivers, etc. to allow catheter controller 62 to communicate with contrast media controller 64 and/or inflation controller 66.

Figure 10:
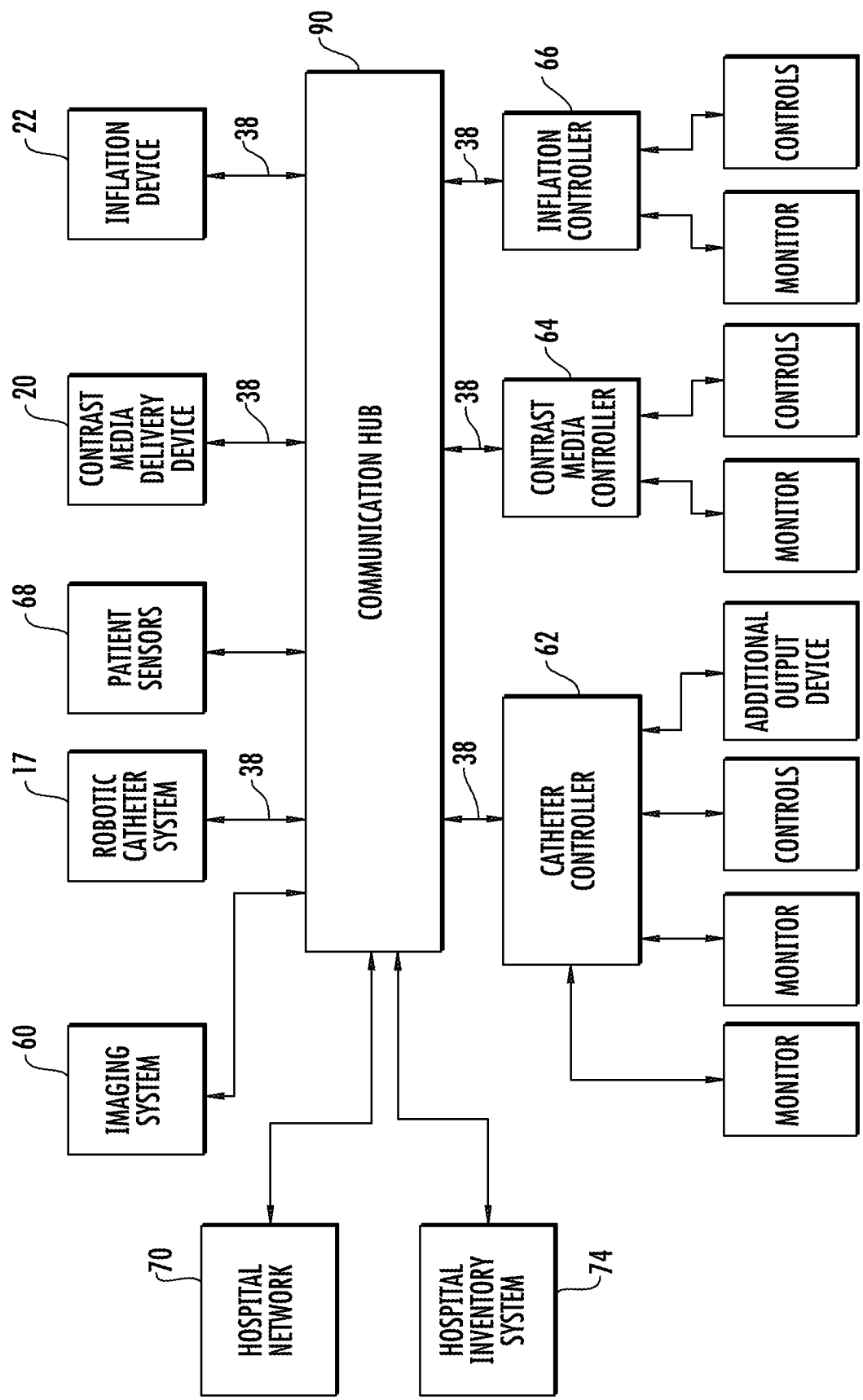
FIG. 10 is a block diagram of a catheter procedure system having a communication hub according to an exemplary embodiment.

In another embodiment, shown in FIG. 10, catheter procedure system 10 may include a communication hub 90. Controllers 62, 64, and 66 and robotic catheter device 17, contrast media delivery device 20, and inflation device 22 may be communicably coupled to communication hub 90 via communication links 38. In this embodiment, communication hub 90 includes one or more communication interfaces for establishing connection to communication links 38. Communication hub 90 includes software and/or hardware to facilitate communication between controllers 62, 64, 66, robotic catheter device 17, contrast media delivery device 20, and inflation device 22. Communication hub 90 may provide a single communication unit able to facilitate communication between controllers 62, 64, and 66, robotic catheter device 17, contrast media delivery device 20, and inflation device 22 of different makes, models, etc. In one embodiment, communication hub 90 includes an identification and compatibility module, such as module 86, discussed above. Further, as shown in FIG. 10, communication hub 90 may also be configured to facilitate communication between controllers 62, 64, and 66 and the imaging system 60, patient sensors 68, hospital network 70, and hospital inventory system 74 via communication links 38. In another embodiment, the monitors, controls, and additional output devices associated with each controller may communicate through communication hub 90 via communication links 38.

Figure 11:
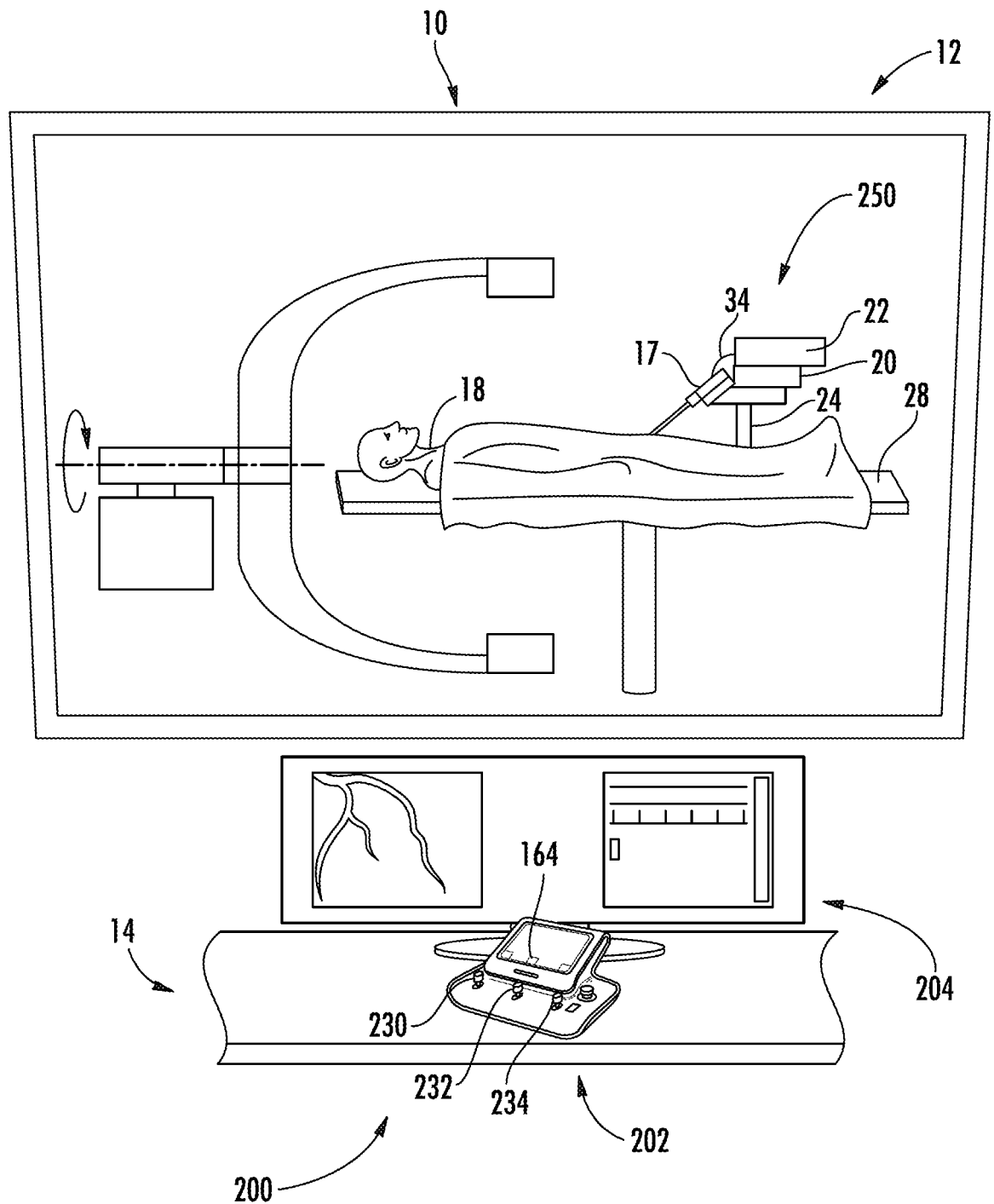
FIG. 11 is a perspective view of a catheter procedure system according to another exemplary embodiment.
Figure 12:
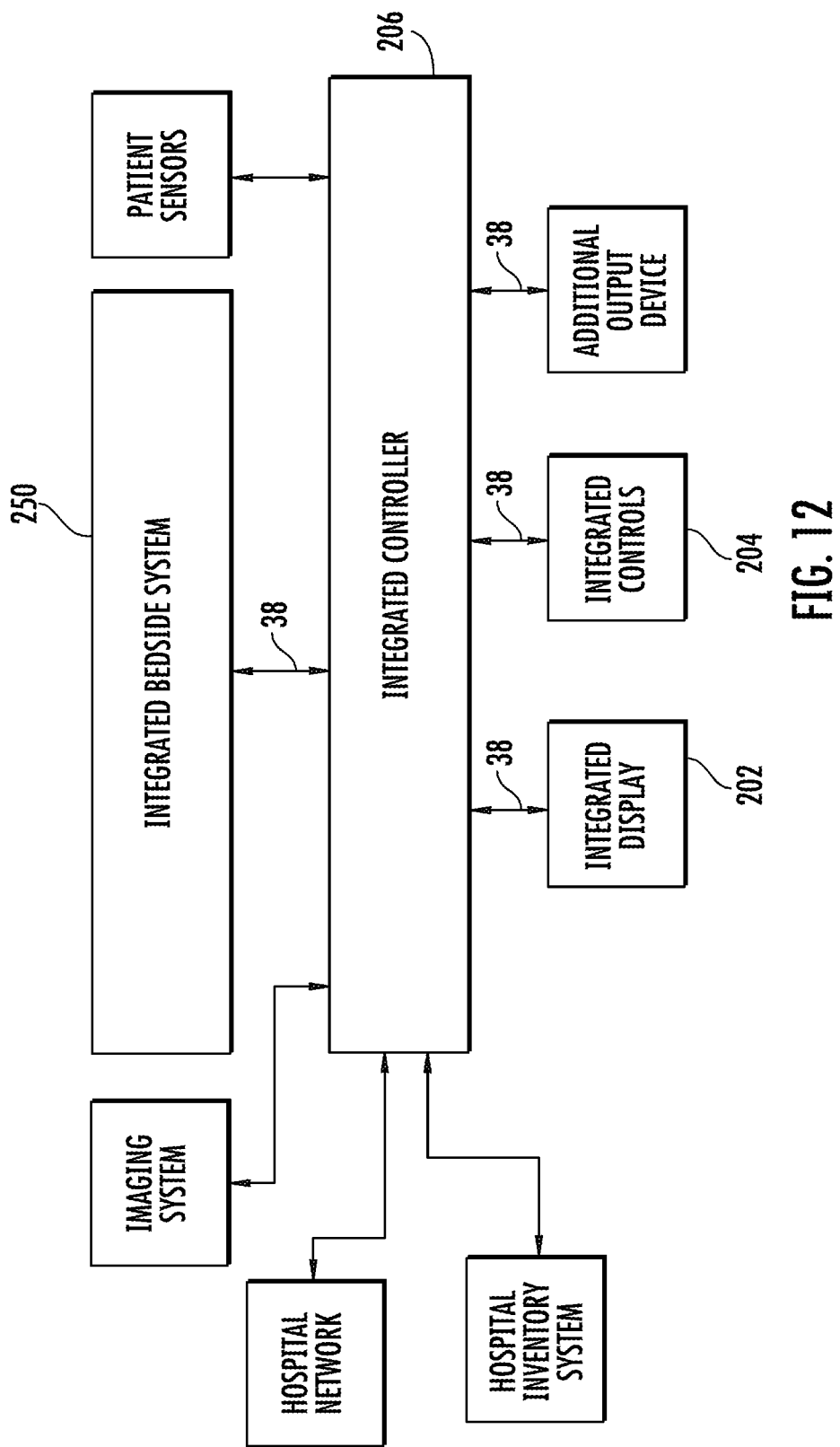
FIG. 12 is a block diagram of the catheter procedure system shown in FIG. 11 according to an exemplary embodiment.
Figure 13:
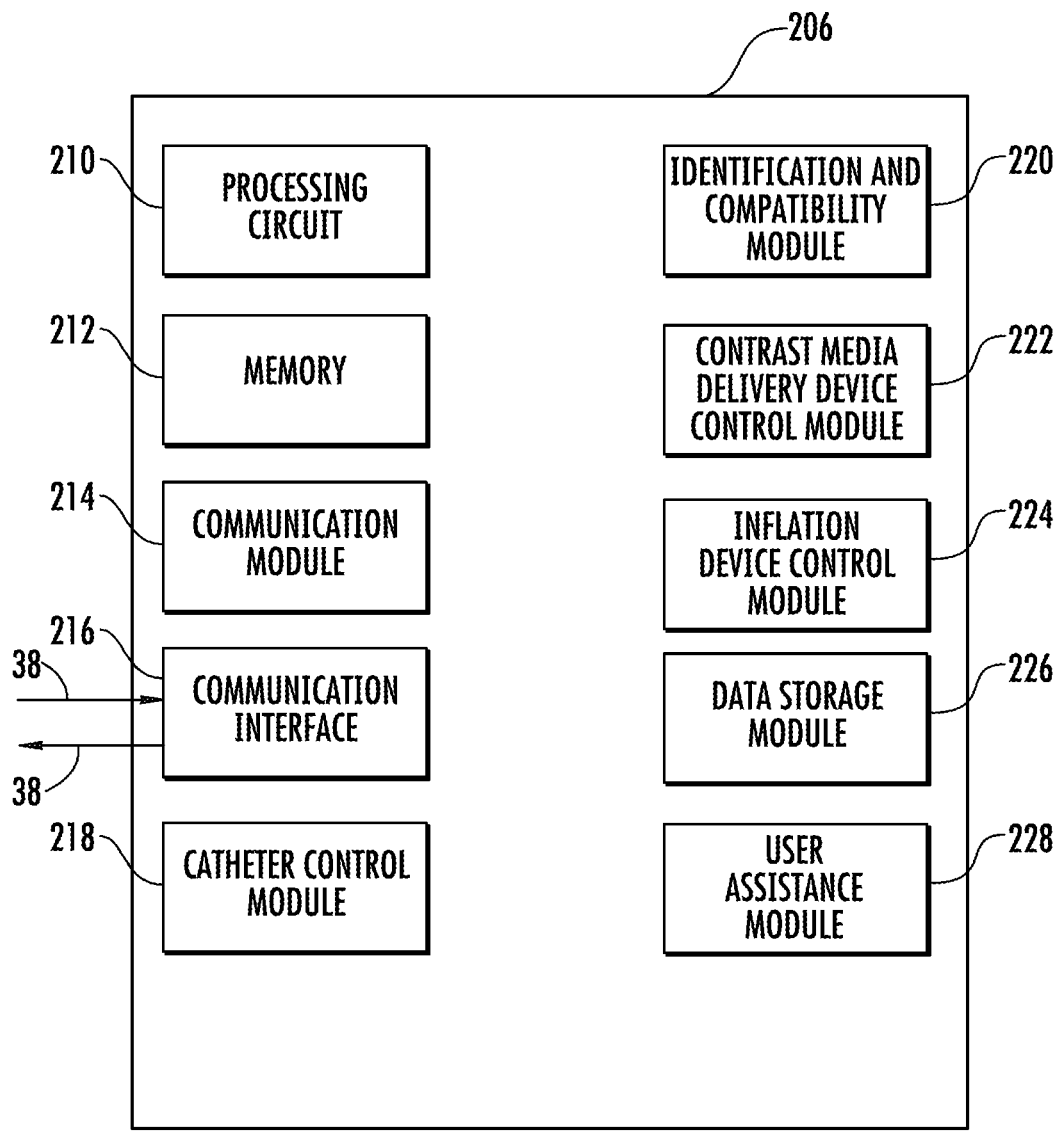
FIG. 13 is a block diagram of a control system according to an exemplary embodiment.

In another embodiment shown in FIGS. 11-13, procedure control system 10 may include a single, integrated user interface 200 located within workstation 14, an integrated control system, shown as integrated controller 206, and an integrated bedside system 250. Integrated bedside system 250 integrates robotic catheter system 17, contrast media delivery device 20, and inflation device 22 into a single unit. As shown in FIG. 11, integrated bedside system 250 utilizes a single support 24. In addition, integrated bedside system 250 may include a single power supply for robotic catheter system 17, contrast media delivery device 20, and inflation device 22. In addition, integrated bedside system 250 may communicate to integrated controller 206 via a single communication link 38.

Integrated user interface 200 and integrated controller 206 provide all of the functionality discussed above regarding interfaces 40, 42, 44, and controllers 62, 64, and 66, respectively. Integrated user interface 200 includes integrated controls 202 and integrated display 204. Integrated controls 202 may include one or more buttons or joysticks, or sets of buttons or joysticks configured to control robotic catheter system 17, contrast media delivery device 20, and inflation device 22 of integrated bedside system 250. In one embodiment, integrated controls 202 includes dedicated controls 230, 232, and 234, assigned to control robotic catheter system 17, contrast media delivery device 20, and inflation device 22, of integrated bedside system 250 respectively. In one embodiment, dedicated controls 230, 232, and 234 may be assigned by the user to control robotic catheter system 17, contrast media delivery device 20, or inflation device 22 as desired by the user. In another embodiment, integrated controller 206 may include a single joystick having multiple switches, buttons, tabs, etc., located such that the user may control robotic catheter system 17, contrast media delivery device 20, and/or inflation device 22 with a single hand. In this embodiment, the user's other hand may be free to perform other tasks, such as controlling imaging system 60, interacting with information (e.g., zooming in, highlighting, etc.) displayed on monitor 204, etc.

Integrated monitor 204 is configured to display all information for a particular procedure, including information related to robotic catheter system 17, to contrast media delivery device 20, and/or to inflation device 22, on a single display device. In one embodiment, integrated monitor 204 includes different areas reserved to display information related to each of the devices to which integrated controller 206 is connected. In another embodiment, integrated monitor 204 may be configured to provide a standardized visual display of information related to each of robotic catheter system 17, contrast media delivery device 20, or inflation device 22.

In another embodiment, integrated bedside system 250 may be operated via the distributed or modular user interfaces 40, 42, 44 and controlled via the distributed or modular controllers 62, 64, and 66. In another embodiment, a portion of integrated bedside system 250 (e.g., only robotic catheter system 17, only contrast delivery device 20, only robotic catheter system 17 and contrast delivery device 20, etc.) may be controlled and operated by integrated controller 206 and operated via integrated user interface 200, and the other components may be controlled and operated via the corresponding dedicated controller and user interface.

In addition, as shown in FIG. 13, integrated controller 206, includes a integrated processor 210, integrated memory 212, integrated communication module 214, integrated communication interface 216, catheter control module 218, identification and compatibility module 220, contrast media delivery device control module 222, inflation device control module 224, data storage module 226, and user assistance module 228. Integrated communication module 214, integrated communication interface 216, catheter control module 218, identification and compatibility module 220, contrast media delivery device control module 222, inflation device control module 224, data storage module 226, and user assistance module 228 are configured to provide the functionality discussed above regarding controllers 62, 64, 66, and/or 340. However, in the embodiment shown, integrated controller 206 provides this functionality while reducing redundant components by utilizing a common processor 210, common memory 212, and a common communication interface 216.

Figure 14:
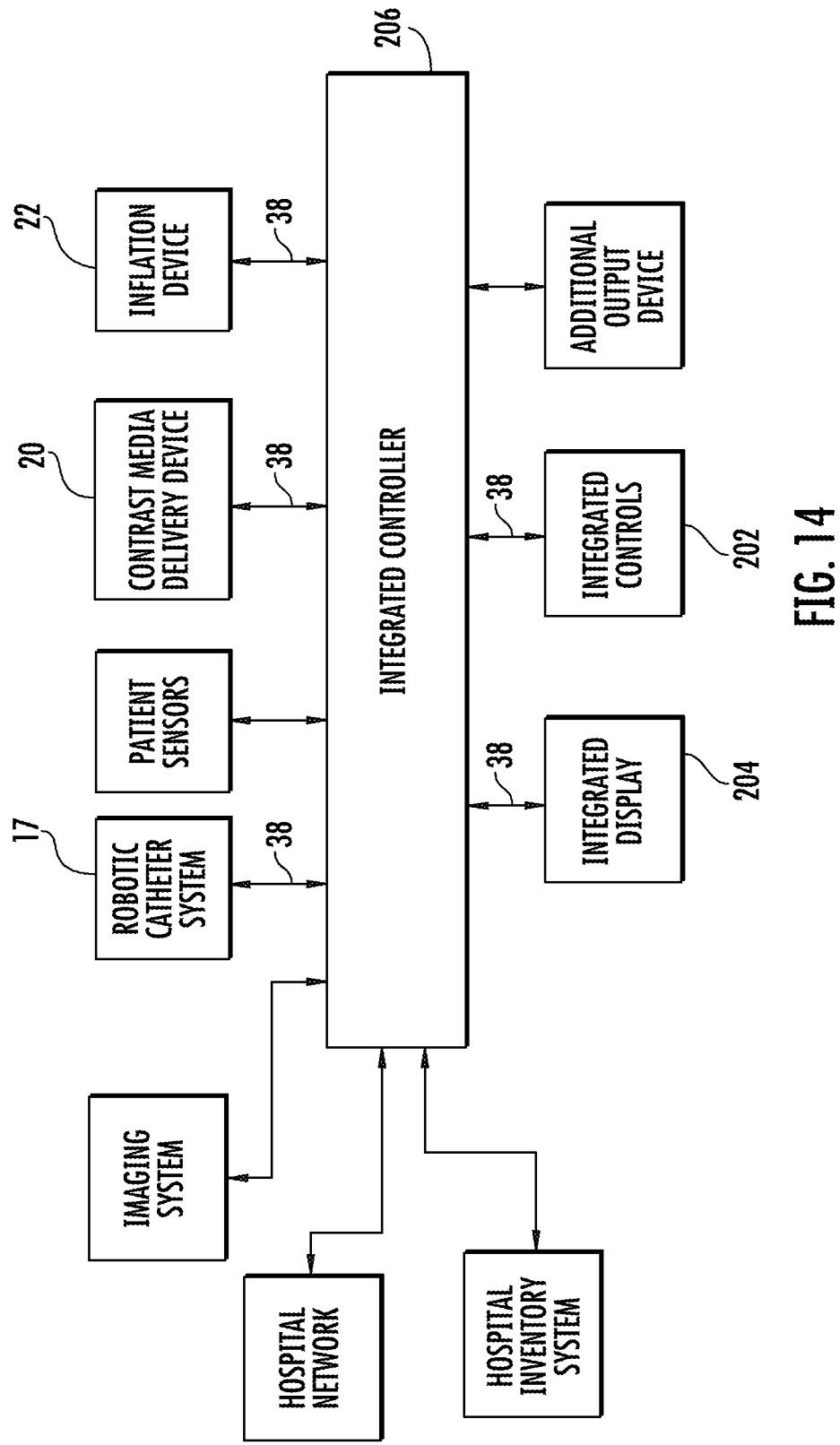
FIG. 14 is a block diagram of a catheter procedure system according to another exemplary embodiment.

In one embodiment shown in FIG. 14, integrated controller 206 is in direct communication with a stand alone robotic catheter system 17, a stand alone contrast media delivery device 20, and a stand alone inflation device 22. Compatibility module 220 allows integrated controller 206 to control different types (e.g., versions, makes, models, etc.) of robotic catheter systems 17, contrast media delivery devices 20 and/or inflation devices 22. Compatibility module 220 identifies the robotic catheter system 17, contrast media delivery device 20 and/or inflation device 22 to which integrated controller 206 has been connected. Following identification, compatibility module 220 activates the proper software, hardware, drivers, etc. to allow integrated controller 206 to communicate with and/or control the particular robotic catheter systems 17, contrast media delivery device 20, and/or inflation device 22.

In this embodiment, contrast media delivery device control module 222 allows manipulation of integrated controls 202 by the user to operate contrast media delivery device 20. Contrast media delivery device control module 222 may also cause data appropriate for a particular procedure to be displayed on integrated monitor 204 during a procedure. Inflation device control module 224 allows manipulation of integrated controls 202 by the user to operate inflation device 22. Inflation device control module 224 may also cause data appropriate for a particular procedure to be displayed on integrated monitor 204 during a procedure.

Figure 15:
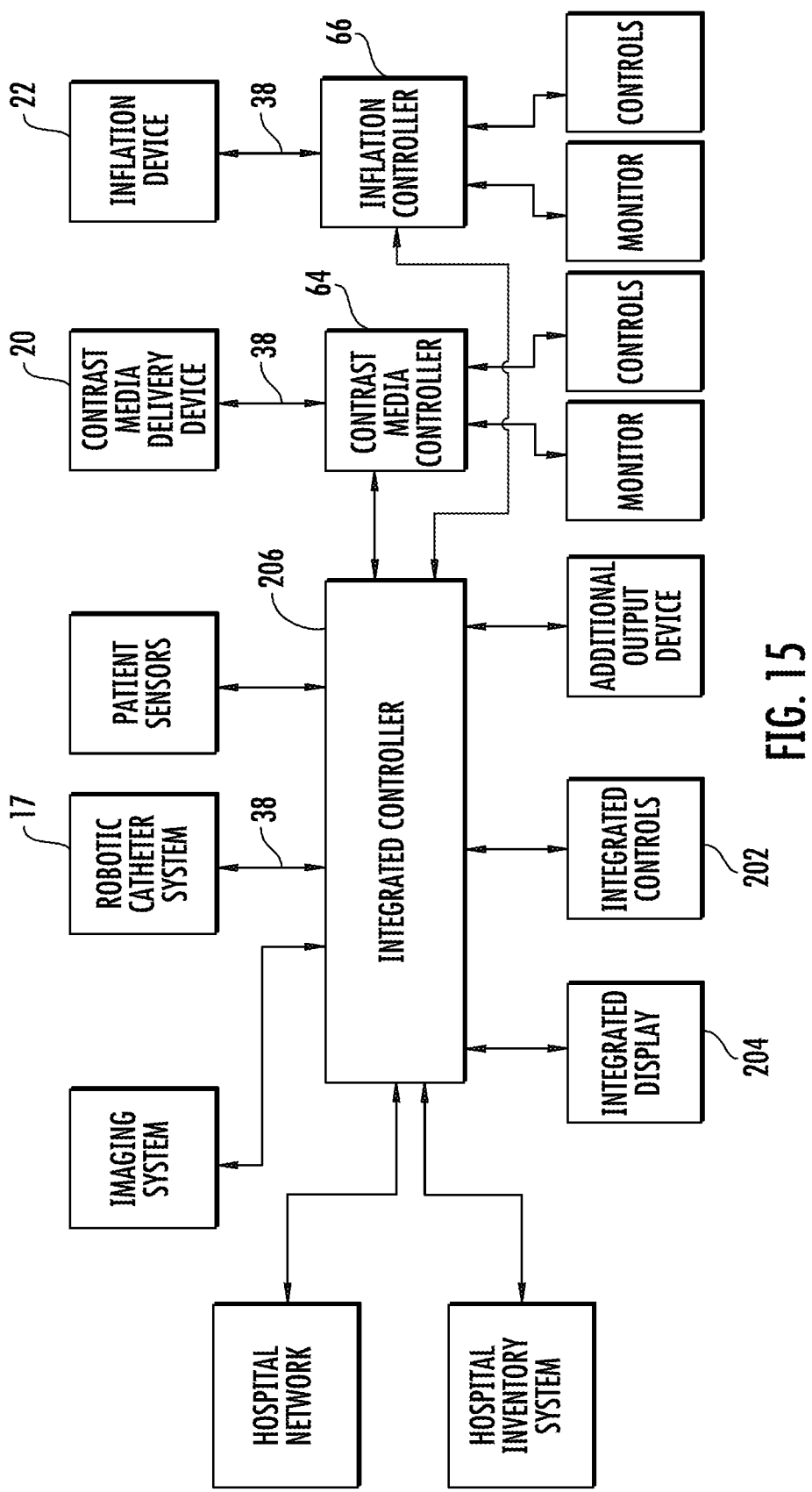
FIG. 15 is a block diagram of a catheter procedure system according to another exemplary embodiment.

In another embodiment shown in FIG. 15, integrated controller 206 includes a module to allow integrated controller 206 to communicate with a stand alone contrast media controller, such as controller 64, and/or with a stand alone inflation controller 66. This embodiment allows integrated controller 206 to function as discussed above regarding controller 62. In this embodiment, integrated controller 206 controls various components of procedure system 10, such as imaging system 60 and robotic catheter system 17, via catheter control module 218. However, in this embodiment, the stand alone contrast media controller 64 and/or the stand alone inflation controller 66 directly control contrast media delivery device 20 and inflation device 22.

In this embodiment, integrated controller 206 is configured to detect whether integrated controller 206 is connected directly to contrast media device 20 and/or inflation device 22 or is connected directly to a stand alone contrast media controller 64 and/or the stand alone inflation controller 66. If integrated controller 206 is connected directly to contrast media device 20 and/or inflation device 22, the contrast media delivery device control module 222 and/or inflation device control module 224 is active to control the devices 20 and 22. If integrated controller 206 is connected directly to a stand alone contrast media controller 64 and/or the stand alone inflation controller 66, the contrast media delivery device control module 222 and/or inflation device control module 224 are inactive allowing the stand alone controllers to control each device. In one embodiment, integrated controller 206 is configured to allow the user to decide whether integrated controller 206 will directly control contrast media device 20 and/or inflation device 22 even if integrated controller 206 is connected to stand alone contrast media controller 64 and/or the stand alone inflation controller 66.

As shown in FIG. 15, in an embodiment in which integrated controller 206 is connected to a stand alone contrast media controller 64 and/or a stand alone inflation controller 66, integrated controller 206 may be configured to allow a user to assign controls 230, 232, and 234 of integrated controls 202 to control contrast media delivery device 20 and/or inflation device 22 as opposed to having the controls (e.g., controls 52, and 56) associated with stand alone contrast media controller 64 and/or a stand alone inflation controller 66 control those devices. This allows the particular user to use the set of controls (e.g., integrated controls 202 or dedicated controls 52 or 56) that the user prefers. This may also provide redundancy in the event that one set of controls breaks or malfunctions.

The exemplary embodiments illustrated in the figures and described herein are offered by way of example only. Accordingly, the present application is not limited to a particular embodiment, but extends to various modifications that nevertheless fall within the scope of the appended claims. In addition, any of the embodiments described herein may incorporate features, elements, modules, subsystems, functionality, etc. of any other exemplary embodiment.

The construction and arrangement of the systems and methods as shown in the various exemplary embodiments are illustrative only. Any of the features, elements, or components of any of the exemplary embodiments discussed above may be used alone or in combination with any of the features, elements, or components of any of the other embodiments discussed above. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. All such modifications are intended to be included within the scope of the present disclosure. Software implementations could be accomplished with standard programming techniques with rule based logic and other logic to accomplish the various connection steps, processing steps, comparison steps and decision steps. Other substitutions, modifications, changes, and omissions may be made in the design, operating conditions and arrangement of the exemplary embodiments without departing from the scope of the present disclosure.

What is claimed is:

1. A catheter procedure system comprising:
   a bedside system, the bedside system comprising:
      a robotic catheter system configured to move a catheter including an expandable percutaneous intervention device, and
      an inflation device configured to cause expansion of the expandable percutaneous intervention device; and
   a control system configured to control both the robotic catheter system and the inflation device,
   wherein the control system controls the robotic catheter system to move the catheter based upon at least a first user input and controls the inflation device to cause expansion of the expandable percutaneous intervention device based upon at least a second user input, and wherein the control system is configured to automatically prevent, slow or stop expansion of an inflatable device when a target point of the inflatable device is not aligned with a landmark, position the landmark over a real time image of a lesion to identify an optimal position of the inflation device relative to the lesion, and allow inflation of the inflatable device based on a realignment of the target point of the inflatable device with the landmark.

2. The catheter procedure system of claim 1, wherein the control system is configured to automatically cause expansion of the expandable percutaneous intervention device at a predetermined rate based on an inflation profile.

3. A remote workstation configured for operating a robotic catheter system, the remote workstation comprising:
a user interface configured to receive at least a first user input and a second user input;
a control system to control the robotic catheter system to move at least one percutaneous device based upon at least the first user input and to expand an expandable percutaneous intervention device based upon at least the second user input; and
a user assistance subsystem operatively connected to the control system configured to provide information to a user to assist the user in the use of the expandable percutaneous intervention device,
wherein the user assistance subsystem alters control of a fluid delivery device, in response to a user input, based upon movement of the at least one percutaneous device in order to synchronize delivery of fluid from the fluid delivery device to the expandable percutaneous intervention device with the movement of the at least one percutaneous device by delivering the fluid prior to movement of the at least one percutaneous device.

4. A catheter procedure system comprising:
a bedside system, the bedside system comprising:
a support structure configured to be coupled to a patient bed;
a robotic catheter system coupled to the support structure and configured to move a catheter including an internal lumen and an expandable percutaneous intervention device;
an inflation device coupled to the support structure and configured to cause expansion of the expandable percutaneous intervention device; and
an inflation conduit connecting the inflation device to the internal lumen of the catheter;
and
a control system in communication with an imaging system configure to capture images of the catheter, the control system configured to control the robotic catheter system, the inflation device and the imaging system;

wherein the control system controls the robotic catheter system to move the catheter based upon at least a user input and controls the inflation device to cause a fluid to flow from the inflation device through the inflation conduit into a lumen of the catheter to automatically cause expansion of the expandable percutaneous intervention device at a predetermined rate based on an inflation profile, and wherein the control system causes the imaging system to automatically capture images at times associated with stages of inflation of the inflation device.

5. The catheter procedure system of claim 4, wherein the control system is configured to cause the imaging system to capture images at times associated with predetermined percentage inflation.

6. The catheter procedure system of claim 5, wherein the control system is configured to cause the imaging system to capture images at times associated with one percent inflation, fifty percent inflation and one-hundred percent inflation.

7. The catheter procedure system of claim 2, wherein the control system includes a user assistance module to identify a size and type of the lesion based on data generated by an imaging system, wherein the user assistance module is configured to identify the inflation profile to treat the identified lesion.

8. The catheter procedure system of claim 1, wherein the expandable percutaneous intervention device is an angioplasty balloon.

9. The catheter procedure system of claim 1, wherein the expandable percutaneous intervention device is a stent.

10. The catheter procedure system of claim 1, wherein a monitor is configured to display information related to the expandable percutaneous intervention device and a position of the catheter.

11. The catheter procedure system of claim 10, wherein the information related to the expandable percutaneous intervention device includes information related to an extent of expansion of the expandable percutaneous intervention device.

12. The catheter procedure system of claim 11, wherein the information related to the extent of expansion of the expandable percutaneous intervention device includes a fluid pressure generated by the inflation device.

13. The remote workstation of claim 3, wherein the fluid delivery device is a contrast media delivery device.

14. The remote workstation of claim 3, wherein the fluid delivery device is a medication delivery device.

15. The catheter procedure system of claim 4, wherein the expandable percutaneous intervention device is an angioplasty balloon.

16. The catheter procedure system of claim 4, wherein the expandable percutaneous intervention device is a stent.

* * * * *